(12) United States Patent
Asnaghi et al.

(10) Patent No.: US 8,507,263 B2
(45) Date of Patent: Aug. 13, 2013

(54) ROTATING BIOREACTOR

(76) Inventors: Maria Adelaide Asnaghi, Meda (IT); Sara Mantero, Milan (IT)

( * ) Notice: Subject to any disclaimer, the term of this patent is extended or adjusted under 35 U.S.C. 154(b) by 106 days.

(21) Appl. No.: 12/621,213

(22) Filed: Nov. 18, 2009

(65) Prior Publication Data
US 2011/0033918 A1 Feb. 10, 2011

Related U.S. Application Data

(60) Provisional application No. 61/273,736, filed on Aug. 7, 2009.

(51) Int. Cl.
*C12M 1/00* (2006.01)
*C12M 3/00* (2006.01)

(52) U.S. Cl.
USPC .............. 435/289.1; 435/284.1; 435/297.2; 435/297.4; 435/307.1

(58) Field of Classification Search
USPC .......... 435/289.1, 284.1, 297.2, 297.4, 307.1, 435/297.1
See application file for complete search history.

(56) References Cited

U.S. PATENT DOCUMENTS

| | | | |
|---|---|---|---|
| 4,988,623 A | 1/1991 | Schwarz et al. | |
| 5,792,603 A | 8/1998 | Dunkelman et al. | |
| 5,843,781 A | 12/1998 | Ballermann et al. | |
| 5,928,945 A | 7/1999 | Seliktar et al. | |
| 6,001,643 A | 12/1999 | Spaulding | |
| 6,008,049 A * | 12/1999 | Naughton et al. | 435/395 |
| 6,099,730 A | 8/2000 | Ameer et al. | |
| 6,416,995 B1 * | 7/2002 | Wolfinbarger | 435/289.1 |
| 6,537,567 B1 | 3/2003 | Niklason et al. | |
| 6,753,181 B2 | 6/2004 | Atala | |
| 6,962,814 B2 * | 11/2005 | Mitchell et al. | 435/402 |
| 7,371,400 B2 | 5/2008 | Borenstein et al. | |
| 2004/0171143 A1 * | 9/2004 | Chin et al. | 435/287.2 |
| 2004/0219659 A1 * | 11/2004 | Altman et al. | 435/284.1 |
| 2006/0258004 A1 * | 11/2006 | Kosnik et al. | 435/396 |
| 2008/0260831 A1 | 10/2008 | Badylak et al. | |

(Continued)

FOREIGN PATENT DOCUMENTS

| WO | WO 00/34442 A2 | 6/2000 |
|---|---|---|
| WO | WO 2011/034627 A2 | 3/2011 |
| WO | WO 2011/062621 A2 | 5/2011 |

OTHER PUBLICATIONS

Asnaghi, M. et al. "A double-chamber rotating bioreactor for the development of tissue-engineered hollow organs: From concept to clinical trial" Biomaterials, (29): 5260-9, Oct. 2009.

(Continued)

*Primary Examiner* — Michael Marcheschi
*Assistant Examiner* — Shanta G Doe
(74) *Attorney, Agent, or Firm* — Wolf, Greenfield & Sacks, P.C.

(57) ABSTRACT

Articles and methods for growing tissues and organs using bioreactors, including rotating bioreactors, are provided. In some embodiments, a bioreactor is configured to provide a first and second chamber, such as an inner and an outer chamber, respectively. The chambers may be co-axially arranged with respect to each other. A wall of the bioreactor defining the two chambers may be formed at least in part from a scaffold derived from a length of a hollow or tubular tissue or organ. Such a bioreactor can be used to form biocompatible structures for tissue engineering and organ replacement, such as cellular tissues, organ-like structures, and/or complete organs, within the bioreactor.

13 Claims, 3 Drawing Sheets

(56) References Cited

U.S. PATENT DOCUMENTS

| | | |
|---|---|---|
| 2009/0075360 A1 | 3/2009 | Ho et al. |
| 2009/0181448 A1* | 7/2009 | Fan et al. .................. 435/284.1 |
| 2013/0041265 A1 | 2/2013 | Sostek et al. |

OTHER PUBLICATIONS

Bayoussef Z., Shakesheff K.M. Aggregation of cells using biomaterials and bioractors. In: Polak J, ed. *Advances in Tissue Engineering*. London: Imperial College Press: 2008: 313-331.

Macchiarini, P. et al. "Clinical transplantation of a tissue-engineered airway," Nov. 19, 2008.

Mather, M. et al. "Meeting the needs of monitoring in tissue engineering," Regenerative Med. (2007) 2(2), pp. 145-160.

Matsuura, T. "Bioreactors for 3-dimensional high-density culture of human cells," Human Cell 2006; 19: pp. 11-16.

Pörtner, R., Giese, C. An Overview on Bioreactor Design, Prototyping and Process Control for Reproducible Three-Dimensional Tissue Culture. In: Marx, U., Sandig, V., ed. *Drug Testing in vitro*. 2007: 53-78, ISBN 9783527314881.

Rolfe, P. "Sensing in tissue bioreactors," Meas. Sci. Technol., 17 (2006) pp. 578-583.

Singh, V. "Tech Focus" Prognosticating the Future of the Bioreactor; Specific Demands Will Impact the Ongoing Evolution of this Device, Genetic Engineering & Biotechnology News, Jan. 15, 2008, vol. 28, No. 2.

* cited by examiner

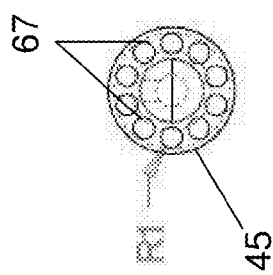
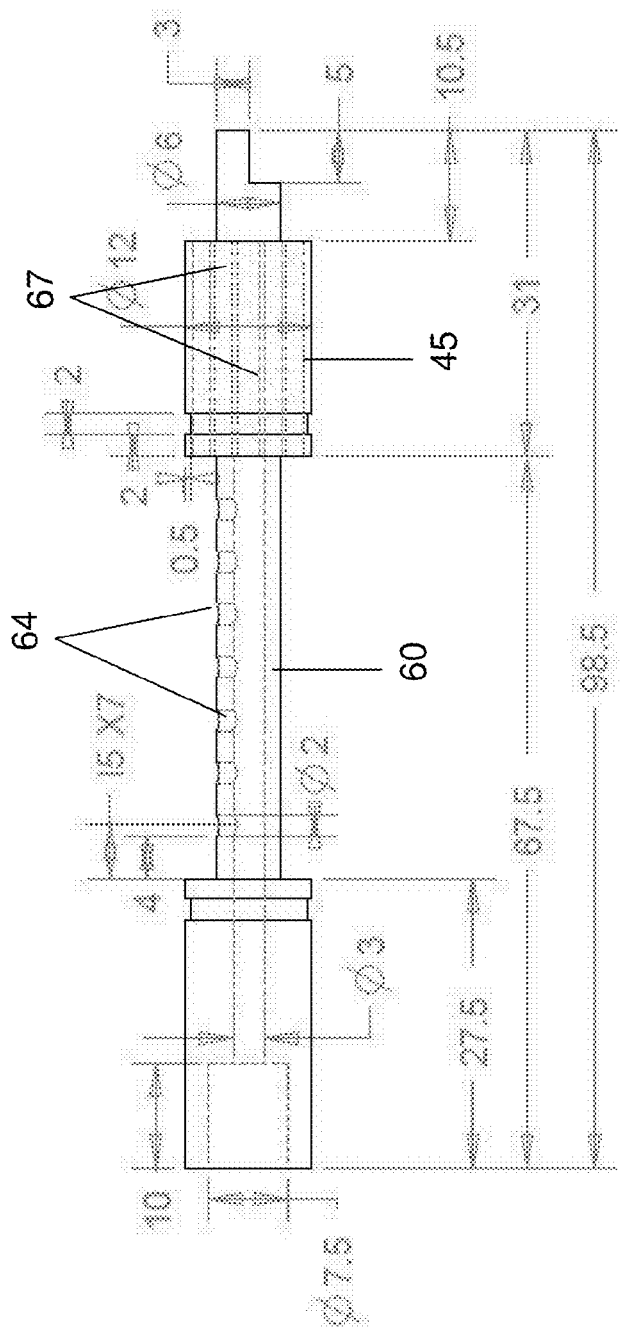
FIG. 3B
FIG. 3A

ROTATING BIOREACTOR

RELATED APPLICATIONS

This application claims priority to U.S. Provisional Application Ser. No. 61/273,736, filed Aug. 7, 2009, the entire contents of which is incorporated herein by reference for all purposes.

FIELD OF INVENTION

The present invention relates generally to articles and methods for growing tissues and organs, and, more specifically, to growing tissues and organs using rotating bioreactors.

BACKGROUND

Bioreactors are important for growing cells, tissues, and organs, as they can enable reproducible and controlled changes to be made in specific environments. Although certain bioreactors for growing cells, tissues, and organs are known, improvements in bioreactor design and/or control would be beneficial.

SUMMARY OF THE INVENTION

The present invention relates generally to articles and methods for growing tissues and organs, and, more specifically, to growing tissues and organs using rotating bioreactors. In some embodiments, the articles and methods can be used to form biocompatible structures for tissue engineering and organ replacement. The subject matter of the present invention involves, in some cases, interrelated products, alternative solutions to a particular problem, and/or a plurality of different uses of one or more systems and/or articles.

In some embodiments, a bioreactor comprises a support upon which cells can be seeded. In some embodiments, the support is a matrix. In some embodiments, the support comprises an axis. In some embodiments, the bioreactor comprises a chamber that contains a support that is capable of rotating. In some embodiments, the support is a hollow tube or chamber. In some embodiments, the support separates an inner chamber from an outer chamber.

In some embodiments, a series of bioreactors is provided. In one embodiment, a bioreactor comprises a vessel and a scaffold defining an outer wall of an inner chamber and an inner wall of an outer chamber, wherein the scaffold is configured to rotate about a central axis. The bioreactor also includes a shaft positioned within the inner chamber, the shaft comprising an opening defining a first inlet for introducing a liquid into the inner chamber. In some embodiments, the bioreactor further includes a first outlet in fluid communication with the inner chamber, and an opening in fluid communication with the outer chamber for introducing and/or removing a liquid from the outer chamber.

In certain embodiments, a bioreactor comprises a vessel and a scaffold removably positioned within the vessel and defining an outer wall of an inner chamber and an inner wall of an outer chamber, wherein the scaffold is configured to rotate about a central axis. The bioreactor includes a first inlet and a first outlet in fluid communication with the inner chamber, and a first sensor coupled to the inner chamber. The bioreactor further includes an opening in fluid communication with the outer chamber for introducing and/or removing a liquid from the outer chamber and a second sensor coupled to the outer chamber.

The bioreactors described above and herein may include a vessel that is removably positioned within the bioreactor. The opening in the shaft defining the first inlet may be radially positioned with respect to a longitudinal axis of the shaft. The bioreactor may further comprise a support structure coupled to the shaft, wherein the support structure comprises an opening defining the first outlet. In some cases, the first chamber and the second chamber are co-axially arranged with respect to each other.

The bioreactors described above and herein may include a variety of components. For example, a bioreactor may comprise one or more mixing elements that are connected to a flange such that they are positioned within the outer chamber and co-rotate with the scaffold to enhance fluid motion and mixing in the outer chamber. In some embodiments, a first pump is in fluid communication with the inner chamber. Additionally or alternatively, a second pump may be in fluid communication with the outer chamber. The bioreactor may comprise one or more sensors for measuring one or more of nutrient composition, nutrient concentration, dissolved oxygen concentration, dissolved carbon dioxide concentration, cell concentration, temperature, pH, and osmolality of the first fluid. Additionally or alternatively, the bioreactor may comprise one or more sensors for measuring one or more of nutrient composition, nutrient concentration, dissolved oxygen concentration, dissolved carbon dioxide concentration, cell concentration, temperature, pH, and osmolality of the second fluid. In some cases, a first and/or second sensor is adapted to measure shear stress or flow rate.

The scaffold positioned in a bioreactor described above and herein may have any suitable shape and/or configuration. In some embodiments, the scaffold is substantially cylindrical. At least a portion of the scaffold may comprise a decellularized tissue construct in some embodiments. The scaffold may be porous or substantially nonporous. The scaffold may be removably positioned within the vessel. The scaffold, in some instances, includes a first cell type and a second cell type. The first cell type may be positioned on the outer wall of the inner chamber and the second cell type may be positioned on the inner wall of the inner chamber. In some embodiments, wherein the scaffold supports and includes a tissue attached thereto. The scaffold may support and include an organ attached thereto. The scaffold may be attached to a rotating flange which is operatively connected to a rotating shaft.

In certain aspects, a series of methods are provided. In one embodiment, a method comprises providing a bioreactor comprising a scaffold defining an outer wall of an inner chamber and an inner wall of an outer chamber, and rotating the scaffold about a central axis in the bioreactor. The method involves subjecting the inner chamber to a first liquid and growing a first cell type on the outer wall of the inner chamber. The method also involves subjecting the outer chamber to a second liquid different from the first liquid and growing a second cell type on the inner wall of the outer chamber, and forming a tissue comprising the first and second cell types.

In another embodiment, a method comprises providing a bioreactor comprising a scaffold defining an outer wall of an inner chamber and an inner wall of an outer chamber, and supplying a first liquid to the inner chamber and submersing a portion, but not all, of the outer wall in the first liquid. The method involves alternately passing portions of the outer wall between the first liquid and a gas, and growing a first cell type on the outer wall of the inner chamber. The method also involves supplying a second liquid different from the first liquid to the outer chamber and submersing a portion, but not all, of the inner wall in the second liquid, alternately passing portions of the inner wall between the second liquid and a gas, and growing a second cell type on the inner wall of the outer chamber.

The methods described above and herein may further comprising seeding a plurality of cells of the first cell type on the outer wall of the inner chamber by rotating the scaffold in a liquid containing the plurality of cells. In some cases, a method includes seeding a plurality of cells of the second cell type on an inner wall of the inner chamber by rotating the scaffold in a liquid containing the plurality of second cells. The method may further include seeding the first and second cell types substantially simultaneously by rotating the scaffold in liquids containing the cells. In some cases, a method includes submersing a portion, but not all, of the outer wall in the first liquid, and alternately passing portions of the outer wall between the first liquid and a gas. The method may comprise submersing a portion, but not all, of the inner wall in the second liquid and alternately passing portions of the inner wall between the second liquid and a gas.

In some embodiments, a method further comprises measuring one or more of nutrient composition, nutrient concentration, dissolved oxygen concentration, dissolved carbon dioxide concentration, cell concentration, temperature, pH, and osmolality of the first and/or second liquids over time. One or more parameters may be measured for the first and second liquids simultaneously. In some embodiments, shear stress is applied to the first and/or second cell types. The method may also include measuring one or more of the degree or existence of cell adherence to the scaffold and fluid shear stress to which cells are exposed. The method may be used to form an artificial organ. The bioreactor and/or scaffold may be one described above and/or in more detail below.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 3A shows a schematic diagram of components of a bioreactor according to one set of embodiments; and FIG. 3B is a cross-sectional view of a component shown in FIG. 3A according to one set of embodiments.

DESCRIPTION

Figure 1A:
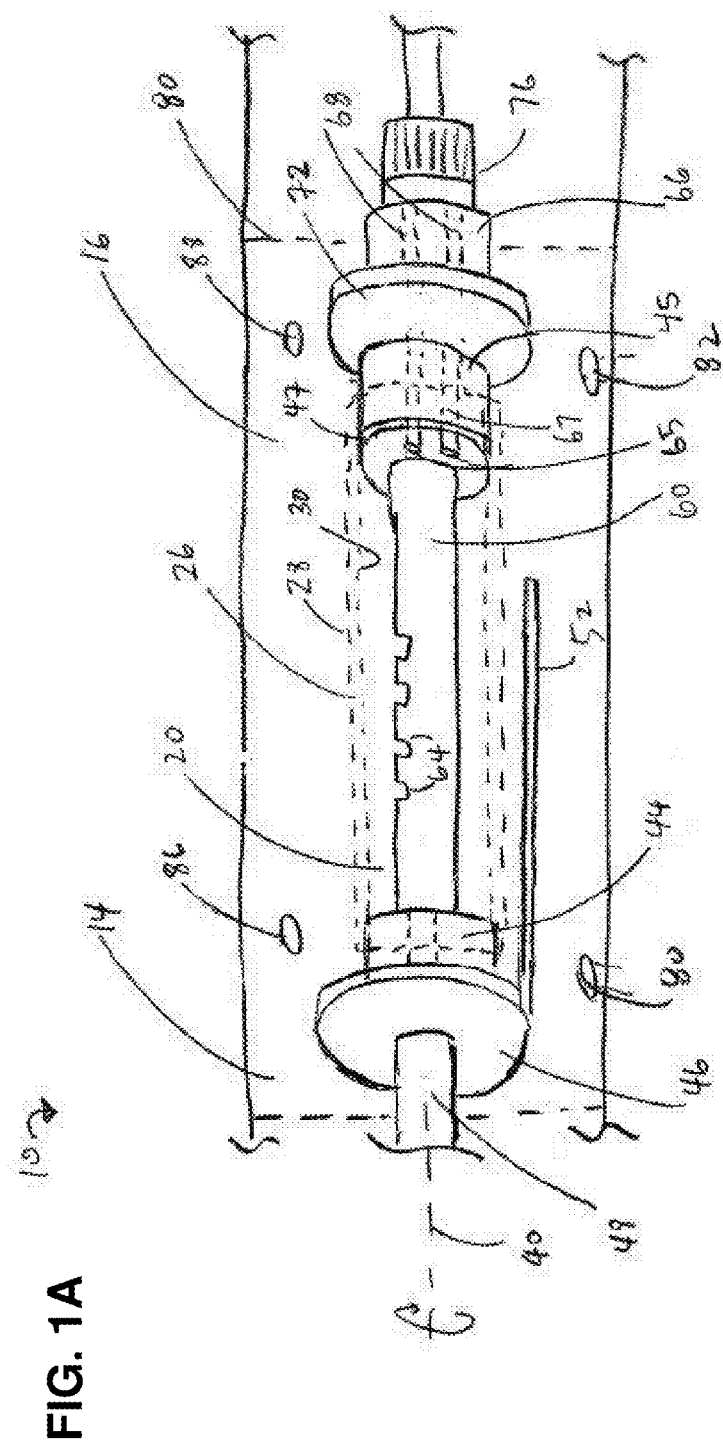
FIG. 1A is a schematic diagram showing a side view of a bioreactor according to one set of embodiments.

The present invention relates generally to articles and methods for growing tissues and organs, and, more specifically, to growing tissues and organs using rotating bioreactors. In some embodiments, the articles and methods can be used to form biocompatible structures for tissue engineering and organ replacement, such as cellular tissues, organ-like structures, and/or complete organs, within the bioreactor. Aspects of the invention may also relate to transplanting cells, tissues, organ-like structures, and/or complete organs into a recipient patient (e.g., a human patient).

In one illustrative embodiment, an inventive bioreactor is configured to provide a first and second chamber, such as an inner and an outer chamber, respectively. The chambers may be co-axially arranged with respect to each other. A cylindrical wall defining an outer cylindrical wall of the inner chamber and an inner cylindrical wall of the outer chamber is configured to rotate about a central axis of the co-axial bioreactor. In some embodiments, the wall is formed at least in part from a scaffold derived from a length of a hollow or tubular tissue or organ, for example including, but not limited to a trachea, an artery, a blood vessel, an esophagus, an intestine, etc., which may or may not be at least partially decellularized. In some embodiments, the wall is formed at least in part from an artificial scaffold, e.g., that may be shaped like an organ structure. In certain, the hollow or tubular tissue or organ construct is attached at or near its ends to a holder configured to rotate with the bioreactor and configured to provide fluid communication between a lumen of the hollow or tubular tissue or organ construct and an environment external to the luminal space of the hollow or tubular tissue or organ construct and in certain cases external to the bioreactor chambers. In certain embodiments, one or more cell types may be seeded and grown on the tubular or hollow tissue or organ construct using the inventive bioreactor for growing tissue in vitro in a form that can be transplanted into a patient.

In certain embodiments, the bioreactor is configured to include a first chamber and a second chamber. In some such embodiments, the bioreactor is configured and utilized to culture a first cell type in the first chamber and a second cell type in the second cell chamber. The bioreactor and an associated control system may be constructed and arranged to provide different culture conditions and/or operating parameters in the first chamber and the second chamber. Such differentially provided controlled parameters/conditions may include, but are not limited to culture media type, nutrient composition and concentration, dissolved oxygen concentration, dissolved carbon dioxide concentration, cell concentration, degree or existence of cell adherence to a substrate, temperature, media movement/fluid shear stress to which cells are exposed, pH, osmolality, etc. Such parameters can be measured over time to monitor viability and/or growth. Advantageously, by exposing a hollow or tubular tissue or organ to at least two different chambers of a bioreactor, in which parameters in each of the chambers can be independently controlled, complex tissue and organ architectures can be formed.

Figure 1B:
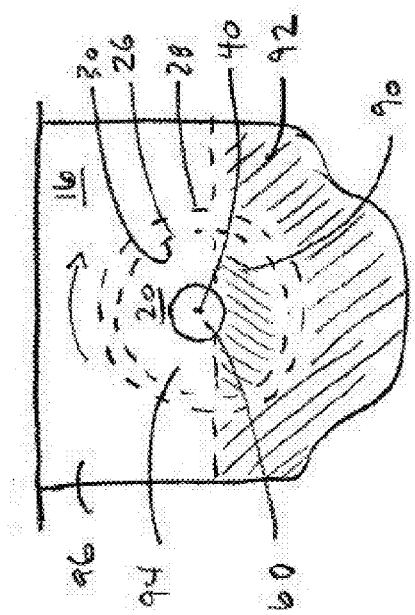
FIG. 1B is a schematic diagram showing a cross-sectional view of the bioreactor illustrated in FIG. 1A according to one set of embodiments.
Figure 2A:
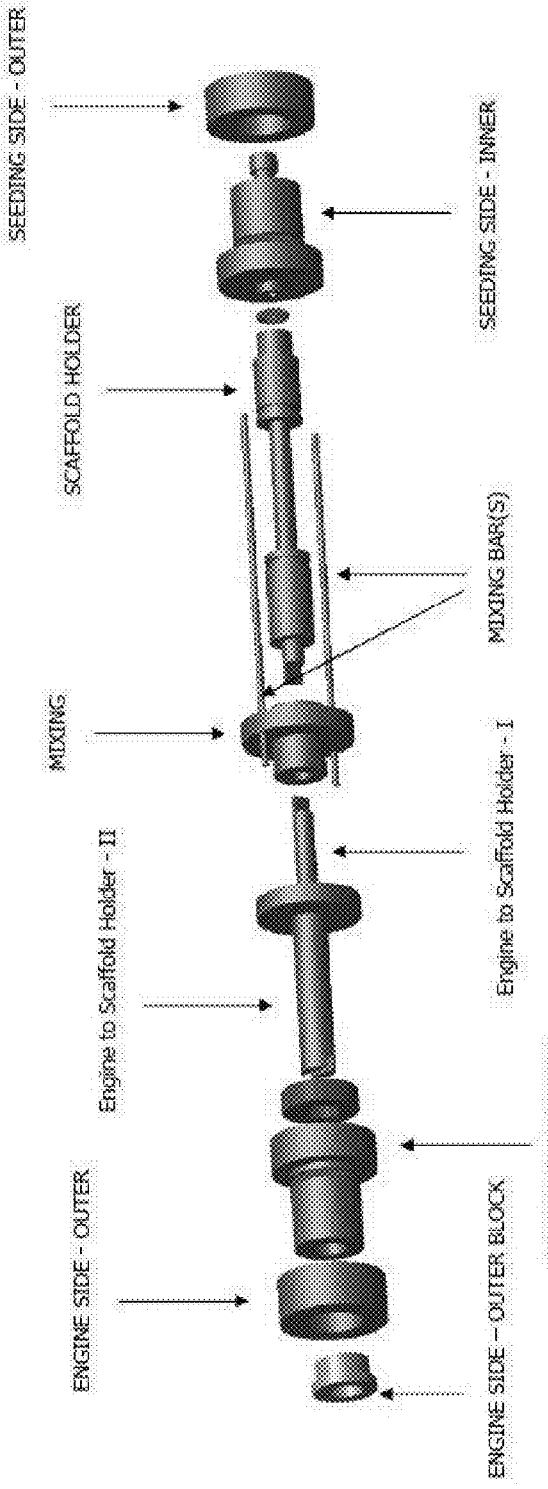
FIG. 2A shows a schematic diagram of a bioreactor including various components according to one set of embodiments.
Figure 2B:
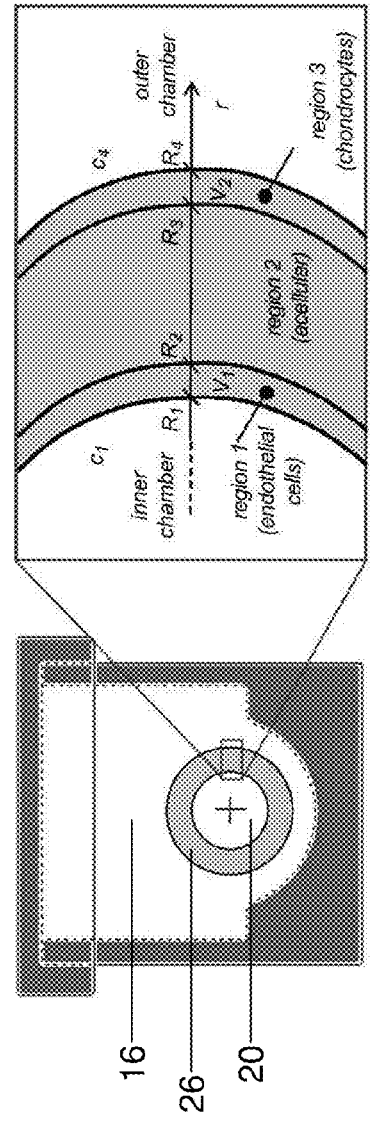
FIG. 2B is a schematic diagram showing a cross-sectional view of a bioreactor according to one set of embodiments.

Non-limiting examples of a bioreactor of the invention are provided in FIGS. 1-3 and in Examples 1-4. FIGS. 1-3 illustrate non-limiting examples of a bioreactor showing individual components. FIG. 3 shows specific components of a bioreactor according to one set of embodiments. Examples 1-4 describe non-limiting examples of uses of a bioreactor of the invention for growing tissue in vitro in a form that can be transplanted into a patient.

It should be appreciated that in some embodiments, aspects of the invention relate to a complete bioreactor (e.g., as illustrated in the Figures and Examples). However, in some embodiments, the invention provides one or more of the component parts, or kits including such component parts. For example, embodiments of the invention may be a chamber, a support structure (e.g., a cellular support structure such as one having an axis and capable of rotating along the axis), a support structure that is hollow, a support structure that has a particular configuration of inlet(s) and outlet(s), a support structure that can be isolated from the chamber, and any one or more of the component parts (e.g., as illustrated by the non-limiting examples of component parts described and shown in the Figures and Examples), and kits including such component parts.

FIG. 1A shows a side view of a schematic diagram of a bioreactor according to one set of embodiments. Bioreactor 10 includes a vessel 14 comprising an outer chamber 16 and an inner chamber 20. As shown in this illustrative embodiment, a scaffold 26 is positioned between the outer and inner chambers. As such, an outer wall 28 of the scaffold defines an inner wall of outer chamber 16, and an inner wall 30 of the scaffold defines an outer wall of inner chamber 20. In such and other embodiments, the outer and inner chambers of the bioreactor can be physically separated from one another by at least one boundary in the form of a scaffold or other structure for promoting cellular growth. Such a structure may comprise a biological material including cells, tissue(s) and/or organ(s) as described herein. For example, the scaffold may support and include a tissue and/or an organ attached thereto in some embodiments.

Although a scaffold in the form of a cylindrical wall is shown in FIG. 1A, other shapes and configurations of scaffolds can be used in bioreactors described herein. Different scaffolds are described in more detail below. It should also be appreciated that where a scaffold is disclosed herein, any suitable structure for seeding, growing, supporting, or maintaining cells, tissues and/or organs may be used. For example, in some embodiments a scaffold derived from a partial or whole organ can be positioned in the bioreactor and may benefit from aspects described herein. In some embodiments, a scaffold is prepared from a decellularized organ or tissue structure. In some embodiments, a scaffold is prepared from a synthetic material (e.g., a biocompatible polymer) that is shaped to support an organ or tissue structure of interest.

As shown illustratively in FIGS. 1A and 1B, the outer and inner chambers may be co-axially arranged with respect to each other and may align along axis 40. The scaffold may be operatively connected to portions of the bioreactor such that the scaffold rotates about axis 40. This rotation can facilitate the generation of fluid motion in the outer and inner chambers. For example, as described in more detail below with respect to FIG. 1B, inner chamber 20 may contain a first fluid 90 suitable for growing a first cell type, and outer chamber 16 may contain a second fluid 92 for growing a second cell type. The first and second fluids may fill a portion, but not all, of the volume of the first and second chambers, respectively, which can allow oxygenation of the fluids. By exposing a scaffold to at least two different chambers of a bioreactor, in which parameters in each of the chambers can be independently controlled, complex tissue and organ architectures can be formed.

In general, as used herein, a component of an inventive system that is "operatively associated with" or "operatively connected to" one or more other components indicates that such components are directly connected to each other, in direct physical contact with each other without being connected or attached to each other, or are not directly connected to each other or in contact with each other, but are mechanically, electrically (including via electromagnetic signals transmitted through space), or fluidically interconnected so as to cause or enable the components so associated to perform their intended functionality.

As shown in the illustrative embodiment of FIG. 1A, scaffold 26 may be attached to a support structure such as rotating flange 44. The rotating flange may be operatively connected to a second flange 46, which in turn is operatively connected to a rotating shaft 48. Shaft 48 may be driven by an external motor or other suitable device. It should be appreciated that other configurations for operatively connecting a support structure to a rotating shaft are possible and that the particular configuration shown in FIG. 1A is not limiting.

A support structure such as flange 44 may have any suitable shape and/or configuration, and can be formed of any suitable material for supporting the scaffold or other structure mounted on the support. For example, as shown in the illustrative embodiment of FIG. 1, flange 44 may have a shape and/or configuration that is complementary to an opening of scaffold 28 for supporting the scaffold. In certain embodiments, flange 44 and/or scaffold 26 is deformable such that when flange 44 is inserted into an opening of the scaffold, a portion of the flange conforms to the shape of the scaffold. In other embodiments, securing means such as an o-ring, clamp, elastic support, ring or annuli, or any other suitable structure can be used to help secure a scaffold onto a support structure. Surgical suturing and/or the use of biocompatible adhesives can also be used alone or in combination with other methods described herein. A securing means may be present at the ends of a scaffold and/or in between (e.g., near a central portion of the scaffold). In some cases, the securing means can create a resistance to further movement of the scaffold relative to the support structure.

It should be appreciated that flange 44 or other support structure can be connected to scaffold 26 directly, or via an intervening article. For example, an opening of the scaffold may be attached to a rod, ring, or other device that provides suitable connection and/or additional support for the scaffold, such that the scaffold can be mounted onto flange 44 via such a device. In some cases, a portion of the scaffold itself or the intervening article has a shape and/or configuration that facilitates handling of the scaffold by a user, facilitates connection of the scaffold to a flange or other component of the bioreactor, and/or facilitates positioning or connection of the scaffold to the body of a recipient. For instance, one or more portions (e.g., ends) of the scaffold may include a handle, rod, ring, flared or tapered ends, combinations thereof, or other suitable shape and/or configuration. A tubular structure may, for example, have flared or tapered ends which can facilitated insertion and/or attachment of the structure to a component of a bioreactor, as well as to the body of a recipient. Such a component that facilitates handling and/or connection of the scaffold may be formed of the same material or a different material as the portion of the scaffold used for growing a tissue or organ. In some cases, such a component comprises a cell resistant material so that fewer cells grow on these portions. In some instances, such components are biodegradable or resorbable after being implanted into a recipient.

Additionally, although FIG. 1A shows a support structure coupled to the scaffold via an opening of the scaffold, a support structure may be coupled to other portions in other embodiments. For instance, a support structure may be coupled to an exterior surface of a scaffold, an interior surface of a scaffold, a branching portion of a scaffold (e.g., with one or more connectors at a first end and one or more connectors at a second end), a base of a scaffold (optionally with gravitational support), combinations thereof, and by other suitable means.

As illustrated in FIG. 1A, flange 44 may be operatively connected to a shaft 60 positioned within inner chamber 20. The shaft may be hollow or tube-like, and may allow the introduction of fluids (e.g., liquids and/or gases) into the inner chamber via one or more openings 64, which can serve as an inlet to the inner chamber. Openings 64 may be the same or different, and may allow one or more fluids to be introduced into the inner chamber (e.g., one opening for introducing a liquid, and a different opening for introducing a gas). Optionally, the inlets and/or outlets described herein may be operatively associated with one or more valves, filters, pumps, controllers, and/or electronics (e.g., sensor electronics, electronic interfaces, and pressurized gas controllers) or other devices for controlling or modulating fluid flow, which may be provided in a kit along with the bioreactor. For example, openings 64 may include a valve, membrane, or other suitable device to allow selective, intermittent, and/or continuous fluid communication between the interior and exterior portions of the shaft. In certain embodiments, as described in more detail below, flow of fluids through one or more openings can allow the cells on the inner wall of the scaffold to be subjected to laminar flow or other flow conditions that are beneficial for cell, tissue, and/or organ growth.

As illustrated in FIG. 1A, openings 64 are radially positioned with respect to the longitudinal axis of the shaft and can define at least one inlet to inner chamber 20. In other embodiments, however, an inlet to the inner chamber may be positioned at an end of shaft 60 (i.e., longitudinally with respect to the axis of the shaft). For example, in one embodiment shaft 60 does not extend from flange 44 to flange 45, but may only extend a portion of such a distance. In some such embodiments, shaft 60 may have an opening at an end portion that can operate as an inlet to the inner chamber. In yet other embodiments, an inlet to the inner chamber may be operatively associated with a portion of flange 44. For example, one or more openings may be formed in flange 44. Tubing and other components can also be used to introduce fluids into the inner chamber. Other configurations of inlets are also possible.

One or more outlets may also be associated with the inner chamber. As shown in the exemplary embodiment of FIG. 1A, flange 45, which may be used as a support structure for another portion of the scaffold, includes openings 65 that lead to channels 67. One or more channels 67 may be in fluid communication with one or more channels 68, which can allow fluids from the inner chamber to exit the device. In instances where flange 72 is absent, channels 67 and channels 68 may be the same channels. In one set of embodiments, the one or more openings may include a valve or other suitable structure such as a membrane or other device to allow selective, intermittent, and/or continuous fluid communication between the interior and exterior portions of the inner chamber. In other embodiments, fluids may enter into channels 67 by rotating flange 45 with respect to portion 47, thereby aligning channel portions 67 with openings 65. This can be done manually or automatically by, for example, pulling or rotating section 76, which is positioned exterior to the inner and outer chambers. In other embodiments, openings 64 may be used as outlets in addition or alternatively to being used as inlets to the inner chamber. One particular example of inlets and outlets that are associated with the inner chamber is shown in FIGS. 3A and 3B.

Where a flange, shaft, or other component is positioned between the inside and outside of a chamber or vessel, the location where the component exits the chamber or vessel may be maintained in a sterile condition. For instance, internal and/or external rotating seals may be used to maintain a sterile seal. By maintaining such a sterile seal, contamination caused by the component, such as from the external environment, may be reduced or avoided.

In certain embodiments, one or more inlets and outlets of the inner chamber can be fluidically connected with one another to form a closed-loop or semi-closed loop system. Similarly, one or more inlets and outlets of the outer chamber can be fluidically connected with one another to form a closed-loop or semi-closed loop system.

Advantageously, the configurations described herein can allow fluids to be removed (and/or introduced) into an inner chamber without the need to remove the scaffold from the bioreactor. Accordingly, the scaffold and any cells, tissues or organs grown thereon can be kept in a sterile environment throughout the seeding, growing, and/or maintaining process.

Also shown in FIG. 1A are an optional inlet 80 and an optional outlet 82, which can be formed in the vessel and can facilitate more convenient introduction and removal of a liquid and/or gas from outer chamber 16. The vessel may have any suitable number of inlets and any suitable number of outlets which may depend on the number and types of fluids being introduced and removed from the vessel. The inlet and outlet, if present, may be positioned in any suitable location with respect to vessel 14. Tubing may be connected to the inlets and/or outlets to form, for instance, delivery and harvest lines, respectively, for introducing and removing fluids from the vessel. Optionally, the inlets and/or outlets may be operatively connected to one or more valves, filters, pumps, controllers, and/or electronics (e.g., sensor electronics, electronic interfaces, and pressurized gas controllers) or other devices available to one of skill in the art for controlling or modulating fluid flow. Such and other components may be provided in a kit along with the bioreactor.

Additionally or alternatively, the vessel and/or bioreactor may include one or more ports 86 and 88 that can be used for sampling, analyzing (e.g., determining pH and/or amount of dissolved gases in the liquid), or for other purposes. In one embodiment, sources of one or more gases can be connected to one or more ports 86 and 88. The inlet gases may optionally pass through a filter, a flow meter and/or a valve (e.g., a pneumatic actuator), which may be controlled by controller system prior to entering the container.

A bioreactor described herein may include a mixing system for mixing contents of the vessel. In some cases, more than one mixing element may be used, for example, one in each of the inner and outer chambers. The mixing elements being the same or different. In one particular set of embodiments, one or more mixing elements 52, such as rods, paddles, baffles, etc. may be connected to flange 46 (and/or flange 72) such that they are positioned within the outer chamber and co-rotate with the scaffold to enhance fluid motion and mixing in the outer chamber. A mixing element may be mechanically or electromagnetically coupled to a motor. In other embodiments, sufficient mixing can be achieved by passing the scaffold between a liquid and a gas, as described herein. Other mixing systems can also be combined with bioreactors described herein.

A bioreactor described herein may optionally include one or more sensors, such as temperature sensors, for determining a component or a condition within a chamber of the bioreactor. For example, one or more temperature sensors may be used to determine the temperature of a fluid inside an inner and/or outer chamber. One or more pressure sensors may be used to determine the amount of pressure inside an inner and/or outer chamber. One or more flow rate sensors may determine the flow rate of a fluid flowing in an inner and/or outer chamber, e.g., so that a particular flow rate can be maintained. In some embodiments, shear stress sensors such as a diverging fringe shear stress sensor or a micro-pillar shear-stress sensor can be used. Sensors for determining components or conditions of a fluid (e.g., nutrient composition and/or concentration, dissolved oxygen concentration, dissolved carbon dioxide concentration, pH, osmolality) may also be incorporated into the bioreactor. A sensor could also be used to measure cell concentration and/or degree or existence of cell adherence to a substrate.

A sensor may be positioned at any suitable location so long as it is operatively associated with the vessel. In some cases, each of the inner and outer chambers include one or more sensors such as those described above. As such, parameters for monitoring the growth and/or maintenance of cells, tissues, organs, or other entities in the chambers can be determined independently and, in some cases, substantially simultaneously. The one or more sensors may be run continuously, periodically, or in some cases, in response to certain events, such as a threshold level of a nutrient within a liquid in the vessel.

A bioreactor can also include visual aids, such as scales or markers, that can facilitate measurement of the size, length, width of a component in the bioreactor.

A bioreactor may also include a temperature control system for monitoring and/or controlling a temperature of a fluid inside a vessel. The bioreactor may further include a thermocouple and/or a resistance temperature detector for sensing a temperature of the contents inside the vessel. The thermocouple may be operatively connected to the temperature controller to control temperature of the contents in the vessel.

In some cases, sensors or other entities associated with a bioreactor are connected to a sensor electronics module (e.g., through wires, wirelessly, optically, etc.), the output of which can be sent to a terminal board and/or a relay box. Various sensors for controlling and/or monitoring one or more process parameters inside the bioreactor such as, for example, temperature, pressure, pH, dissolved oxygen, dissolved carbon dioxide, mixing rate, and gas flow rate, liquid flow rate, can be used. The results of the sensing operations may be input into a computer-implemented control system for calculation and control of various parameters (e.g., temperature and weight/volume measurements) and for display and user interface. Such a control system may also include a combination of electronic, mechanical, and/or pneumatic systems to control heat, air, and/or liquid delivered to or withdrawn from the vessel as required to stabilize or control the environmental parameters of the process operation. It should be appreciated that the control system may perform other functions and is not limited to having any particular function or set of functions.

The one or more control systems can be implemented in numerous ways, such as with dedicated hardware and/or firmware, using a processor that is programmed using microcode or software to perform the functions recited above or any suitable combination of the foregoing. A control system may control one or more operations of a single chamber of a bioreactor, multiple chambers of a bioreactor, or even multiple (separate or interconnected) bioreactors. The control systems can also be implemented using any of a variety of technologies, including software (e.g., C, C#, C++, Java, or a combination thereof), hardware (e.g., one or more application-specific integrated circuits), firmware (e.g., electrically-programmed memory) or any combination thereof.

In one embodiment, a control system operatively associated with a bioreactor described herein is portable along with the bioreactor itself, and optionally along with any pumps, connectors, and/or sources of fluids. The control system may include, for example, all or many of the necessary controls and functions required to perform a fluidic manipulation (e.g., temperature control, mixing, and performing reactions) in the bioreactor. The control system may be manipulated remotely in some embodiments. Advantageously, such and other portable control systems can be programmed with set instructions, and, if desired, transported (optionally with the bioreactor) and hooked up to the bioreactor, ready to perform a process by an end user. A kit including such and other components may also be provided.

In some embodiments, especially in certain embodiments involving growing a tissue and/or organ in a bioreactor, the vessel containing the scaffold, tissue construct, organ, or other entity is substantially closed, e.g., the vessel is substantially sealed from the environment outside of the vessel except, in certain embodiments, for one or more inlet, outlet and/or access ports that allow addition to and/or withdrawal of contents from the vessel. By maintaining a sterile seal, contamination caused by the component, such as from the external environment, may be reduced or avoided.

In certain embodiments, the bioreactor is designed to allow a support structure such as flanges 44 and 65 (or portions thereof) to be removed from the vessel in order to isolate the scaffold from the chamber. For instance, flanges 44 and 65 may be removably coupled to flanges 46 and 72, respectively. The flanges 44 and 65 may be removably coupled to flanges 46 and 72 (or to another suitable component) by, for example, electromagnetic, magnetic, or mechanic coupling. As such, the scaffold may be removably positioned in the vessel and/or the bioreactor. Removal of the scaffold and optionally other components from a vessel or bioreactor can take place through any suitable means (e.g., through the use of forceps, robots and the like).

In other embodiments, vessel 14 is removably coupled to shaft 48 or other exterior portions of the bioreactor. For instance, the vessel may be positioned within a housing (not shown) to which tubing, ports, electronics, and/or other components are connected. The tubing, ports, electronics, and/or other components can be operatively associated with the vessel (e.g., via fluid-tight seals) when the vessel is positioned within the housing. In such and other embodiments, the vessel can be removed from the housing and transported while being maintained in a sterile environment. In yet other embodiments, an entire bioreactor system is portable and can be transported during or after a desired process.

In some embodiments, a vessel includes a cover that is removably positioned on top of remaining portions of the vessel. The cover may enclose the vessel so as to provide a sterile environment within the vessel. The cover may simply sit on top of the walls of the vessel, similar to how a cover of a petri dish sits on top of the petri dish, or the cover may be attached to the vessel by intervening components such as hinges, seals, locks, magnets, and the like. In other embodiments, a cover is integrally connected to other portions of the vessel. Removal and/or introduction of a component from or into the vessel may take place by removing a panel, an end portion, or other portion of the vessel.

A vessel may have any suitable size for containing a liquid, scaffold, or other entity. For example, the vessel may have a volume from about 0.01 L and about 0.5 L, from about 0.1 L and about 0.5 L, about 0.1 L and about 1 L, about 1 L and about 5 L, and from about 1 L and about 10 L. Smaller and larger volumes are also possible. The volumes may depend on the particular use of the bioreactor (e.g., the size of the scaffold, the particular tissue or organ being grown, etc.).

In bioreactors used for certain types of cell, tissue or organ cultivation, the cell, tissue or organ may require nutrients such as sugars, a nitrogen source (such as ammonia ($NH_3$) or amino acids), various salts, trace metals and oxygen to allow growth, division, and/or maintenance of such components. The amount of nutrients available to cells at any one time depends in part on the nutrient concentration in the liquid culture. Sugars, nitrogen sources, salts, and trace metals may be soluble in a liquid and, therefore, may be readily available by replenishing the cells with fresh liquid media. In some cases, liquids can be introduced into the inner and outer chambers of a bioreactor via one or more inlets described herein. The one or more inlets may be in fluid communication with one or more adjustable pumps, which are connected to sources of fluid containing appropriate combination of nutrients. In embodiments in which the percentage of different components changes depending on the stage of growth, the different components can be added together in real-time to form a media composition suitable for that growth stage. This can be done through a feedback system where one or more sensors measures the composition of the liquid(s) in the inner and/or outer chambers, sends the values to a computer, which then determines what composition of fresh media is needed. After the media is formed, it can be delivered continuously or periodically to the appropriate chamber at a suitable flow rate and volume. Each of the inner and outer chambers can include such a control system for maintaining different growth conditions in the chambers.

Like the other nutrients, even and uniform distribution of oxygen throughout the chambers of a bioreactor may be essential to provide uniform cell, tissue, or organ growth. Poor distribution of oxygen can create pockets of cells deprived of oxygen, leading to slower growth, alteration of the cell metabolism or even cell death. In addition, the presence of salts plus the elevated temperature necessary to grow certain cells, tissues and organs may further reduce dissolved oxygen concentration. Since oxygen may be relatively poorly soluble or "dissolved" in water, it can be delivered to the cells by a supply of gas.

In one embodiment, oxygen is delivered to cells by rotating the scaffold on which the cells, tissues or organs are mounted. As shown in the illustrative embodiment of FIG. 1B, a portion, but not all, of scaffold 26 may be exposed to a first fluid 90 (e.g., a first liquid media) suitable for growing a first cell type in inner chamber 20. Because the volume of the scaffold is not completely filled with the first fluid, inner wall 30 of the scaffold can be simultaneously exposed to a fluid 94 (e.g., a first gas). That is, when the scaffold rotates about axis 40, this can cause portions of the inner wall to alternately pass between a gas and a liquid. This movement can replenished fluid 90 with certain components such as oxygen from fluid 94. Similarly, a portion but not all of outer chamber 16 may be filled with a second fluid 92 (e.g., a second liquid media). When the scaffold rotates about axis 40, this can cause portions of the outer wall 28 of the scaffold to alternately pass between a gas and a liquid, which can allow fluid 92 to be replenished with certain components such as oxygen from fluid 96.

It should be appreciated that in other embodiments, other operating conditions for promoting cell, tissue and organ growth may be appropriate. For instance, in some cases, one or more of the inner chamber(s) and outer chamber(s) are substantially filled with a fluid (e.g., a gas or liquid). In certain cases, at least 25%, at least 50%, at least 75% or at least 90% of the volume of a chamber is filled with a first fluid (e.g., a liquid or a gas), the remaining volume being filled with a second fluid, which may optionally be immiscible with the first fluid (e.g., a gas or a liquid, respectively). Combinations of such volumes are also possible for each of the chambers. Such volumes may be appropriate for at least 25%, at least 50%, at least 75% or at least 90% of the total time of growth of the tissues or cells in the bioreactor.

In other embodiments, oxygen and/or other gases can be introduced into a bioreactor to compensate for depletion of oxygen or other gases. As described herein, a bioreactor may include a port that is dimensioned for connection to different sources of gas, which may be independently controlled. The type of gas, number of ports, and types and configurations of ports of a bioreactor may depend, in part, on the particular processes to be carried out and cells/tissues/organs to be grown. In one embodiment, a bioreactor includes sources for different types of gases such as a dissolved oxygen control gas for controlling the amount of dissolved oxygen in the culture fluid and a pH control gas for controlling the pH of the culture fluid. For example, carbon dioxide may be used to increase solution pH and ammonia may be used to decrease solution pH. In one embodiment, a pH control gas may include a combination of carbon dioxide, ammonia, or other gases to control (e.g., increase or decrease) pH. Each type of gas may be introduced into and/or removed from the culture using different ports that can be independently operated and controlled.

Gases may be introduced continuously, periodically, or in some cases, in response to certain events, e.g., within a bioreactor system and/or within the vessel. For example, gas inlets may be connected to one or more sensors and a control system which is able to monitor the amount of gas introduced, pH, and/or the amount or concentration of a substance in the vessel, and respond by initiating, reducing, or increasing the degree of gas introduction of one or more composition(s) of gases.

As shown in the exemplary embodiment illustrated in FIG. 1, vessel 14 can be operatively associated with a variety of components as part of an overall bioreactor system 10. Accordingly, the vessel may include several fittings to facilitate connection to functional component such as filters, sensors, pumps and mixers, as well as connections to lines for providing reagents such as liquid media and gases.

It should be understood that not all of the features shown in FIGS. 1A and 1B need be present in all embodiments of the invention and that the illustrated elements may be otherwise positioned or configured. Also, additional elements may be present in other embodiments, such as the elements described herein. For example, although FIG. 1A shows a single inner chamber and a single outer chamber, a vessel can include addition inner and/or outer chambers. In certain embodiments, a series of inner chambers and scaffolds can be positioned within an outer chamber. The scaffolds may be mounted on a single shaft in series, or on different shafts in parallel. Each of the inner chambers can have different (or the same) growth conditions, allowing multiple tissues and organs to be grown substantially simultaneously. In other cases, a single scaffold can be exposed to at least 2, 3, 4, 5, or 6 different chambers for growing the same or different cell types across different portions of the scaffold. The parameters in each of the chambers can be independently controlled as described herein to form complex tissue and organ architectures.

Additionally, a bioreactor described herein may include components for increasing safety and/or reproducibility of the bioreactor assembly, scaffold positioning, and/or cell seeding. For instance, bioreactor components that require assembly may be mated with one another through the use of complementary elements (e.g., male/female parts, supports, etc.) that can be configured in only certain orientations. In another example, a bioreactor may include a base to maintain the shaft or the flanges in their positions while positioning the scaffold adjacent the shaft and/or while removing the scaffold from the bioreactor. These and other configurations can simply a user's assembly and/or use of the bioreactor. Other means for enhancing safety and/or reproducibility of assembly are also possible.

In operation, the chamber(s) rotating is useful, in some embodiments, to help ensure a homogeneous mixture of nutrients and also to mix and/or remove waste products to the medium (e.g., in the inner and/or outer chambers). Furthermore, in some embodiments, rotation of the chamber(s) generates shear and/or other physical stress on the cells seeded on the support. For example, a shear flow stress of from about 0.01 to about 500 dynes/cm$^2$, from about 0.01 to about 50 dynes/cm$^2$, from about 1 to about 200 dynes/cm$^2$, from about 1 to about 100 dynes/cm$^2$, from about 1 to about 50 dynes/cm$^2$, or from about 1 to about 25 dynes/cm$^2$ may be applied to the cells. Smaller or larger values of shear stress are also possible. In some embodiments, the use of shear stress aids or promotes cell or tissue growth and/or the formation of cellular tissue with enhanced structural properties (e.g., increased elasticity, tensile strength, etc., or a combination thereof). The use of shear stress can also help to guide cell orientation and/or alignment.

It should be appreciated that the shear stress may be varied depending on the stage of cell/tissue/organ growth. For example, a low shear stress may be appropriate during the seeding of cells to facilitate cell attachment onto a scaffold. The shear stress can then be increased to higher levels after cell seeding. The amount shear stress will also depend on factors such as the size of the tissue or organ, the particular type of tissue or organ, and the particular types of cells being seeded. Furthermore, the amount of shear stress can be varied independently within each of the chambers of a bioreactor. For example, cells in an inner chamber may be subjected to a first shear stress and cells in an outer chamber may be subjected to a second shear stress different than (or the same as) the first shear stress.

In addition to or alternatively to movement of fluid by rotation of the scaffold, cells, tissues and/or organs can be subjected to fluid stress by the flow of fluids across a portion of the scaffold. This fluid stress may be brought about by subjecting all or a portion of the cells, tissues and/or organs to laminar flow, turbulent flow, or other flow conditions. Fluid flow may be continuous, pulsatile, or intermittent at a particular flow volume and/or pressure, or at various flow volumes and/or pressures. For instance, a change in flow profile over time can be achieved (e.g., to increase or decrease volume and/or pressure as function of time) as the tissue becomes more resilient. Furthermore, different portions of the scaffold can be subject to different flow conditions. For instance, inner wall 30 of the scaffold can be subjected to a first set of flow conditions in the inner chamber, and outer wall 28 of the scaffold can be subjected to a second set of flow conditions in the outer chamber. This may be achieved by, for example, the use of one or more inlets associated with flange 44 for flowing fluids across inner wall 30, and the use of one or more inlets across the outer edge of flange 46 for flowing fluids across outer wall 28. The one or more inlets and outlets can be configured to cause fluid flow in substantially one direction, in different directions, at the same time, at different times, or at overlapping times. Advantageously, such and other flow conditions can mimic the natural forces that the cells, tissues and/or organs is subjected to in its natural environment.

In some cases, such and other flow conditions is achieved while the scaffold is rotating about an axis. In other embodiments, the flow conditions are imposed only after the scaffold stops rotating. For example, rotation of the scaffold may take place while cells are being seeded onto the scaffold. After seeding, rotation of the scaffold may cease or be reduced, and the inner and/or outer walls of the scaffold may be subjected to a flow condition described herein.

Fluid flow may also take place across a wall of the bioreactor. For instance, where a scaffold acts as an outer wall of the inner chamber and an inner wall of the outer chamber, the scaffold may include pores or other openings so as to allow fluid flow from the inner chamber to the outer chamber and/or from the outer chamber to the inner chamber. A fluid flow gradient may be established across the pores or other openings of the scaffold. This may help to enhance uniform cell colonization throughout the scaffold thickness and/or to condition cells in the pores of the scaffold. In some cases, specific growth factors or other components can be administered through such and other flows. A fluid flow gradient across the pores of the scaffold may be established while the scaffold is rotating about an axis.

As described herein, fluid may flow in a closed loop (e.g., continuously, periodically or intermittently), a semi-closed loop (e.g., where some fresh media is added continuously, periodically or intermittently while existing media is cycled), or in a non-closed loop. Each of the inner and outer chambers may be associated with closed, semi-closed or non-closed loops which may be controlled independently. Fluid flow can be achieved by using one or more adjustable pumps known to those of ordinary skill in the art to modulate flow rate.

As noted herein, cells, tissues and/or organs may be grown on a scaffold that is positioned within a vessel of a bioreactor described herein. In certain embodiments involving bioreactors having a first and a second chamber, at least first and second chambers of a bioreactor are physically separated from one another by the scaffold.

In growing tissues and/or organs of the body, different types of cells can be arranged proximate a scaffold in sophisticated organizations or architectures that are responsible for the complex functions of the tissue or organ. Thus, architectures having dimensions and arrangements closely related to the natural conditions of the tissue or organ can be formed. The design of the scaffold and the arrangement of cells within the scaffold can allow functional interplay between relevant cells, i.e., between cells cultured on the scaffold and those of the host environment. These factors may also enable appropriate host responses, e.g., lack of blood clotting, resistance to bacterial colonization, and normal healing, when implanted into a mammalian system.

A variety of different scaffolds can be used for seeding, growing, supporting, or maintaining cells, tissues, and organs as described herein. A scaffold can have any suitable shape and may depend on the particular tissue and/or organ to be grown. For example, the scaffold may be substantially tubular, substantially cylindrical, substantially spherical, substantially planar, substantially ellipsoidal, disk-like, sheet-like, or irregularly shaped. The scaffold can also have branching structures, e.g., to mimic arteries, veins, or other vessels. In certain embodiments, at least a portion of the scaffold is hollow.

Scaffolds may be formed of natural and/or artificial materials. Materials used to form scaffolds may be biocompatible, and can include synthetic or natural polymers, inorganic materials (e.g., ceramics, glass, hydroxyapatite and calcium carbonate), composites of inorganic materials with polymers, and gels. All or a portion of a scaffold may be formed in a material that is non-biodegradable or biodegradable (i.e., via hydrolysis or enzymatic cleavage). In some embodiments, biodegradable polyesters such as polylactide, polyglycolide, and other alpha-hydroxy acids can be used to form scaffold. By varying the monomer ratios, for example, in lactide/glycolide copolymers, physical properties and degradation times of the scaffold can be varied. For instance, poly-L-lactic acid (PLLA) and poly-glycolic acid (PGA) exhibit a high degree of crystallinity and degrade relatively slowly, while copolymers of PLLA and PGA, PLGAs, are amorphous and rapidly degraded. A portion of a scaffold that is biodegradable may, in some embodiments, degrade during the growth of cells, tissues and/or organs in the bioreactor. In other embodiments, degradation may take place after implanting the tissue or organ in a recipient.

A scaffold may, in some cases, be formed of a biological material, such as a tissue construct. In certain embodiments, at least a portion of the tissue construct is acellular. In certain embodiments, the at least partially acellular tissue construct comprises tissue that has been decellularized. In the description herein concerning the use of appropriate materials to fabricate scaffolds, those of ordinary skill in the art can select materials, techniques, etc. based upon general knowledge of the art and available reference materials concerning certain techniques for fabrication, in combination with the description herein. In some cases, combinations of natural and artificial materials can be used.

Appropriate systems and techniques for fabricating scaffolds include, but are not limited to, molding, three-dimensional printing (e.g., three-dimensional layering), multi-photon lithography, stereolithography (SLA), selective laser sintering (SLS) or laser ablation, ballistic particle manufacturing (BPM), and fusion deposition modeling (FDM). Other fabrication techniques are also possible.

Scaffolds may be porous or substantially nonporous. In some instances, the wall of a scaffold includes pores having a cross-sectional dimension of less than or equal to 1 mm, less than or equal to 100 microns, less than or equal to 50 microns, less than or equal to 40 microns, less than or equal to 30 microns, less than or equal to 10 microns, less than or equal to 5 microns, less than or equal to 1 micron, or less than or equal to 100 nm. A variety of techniques can be used for introducing porosity into a scaffold. For instance, porosity can be induced by methods such as solution casting, emulsion casting, polymer blending, and phase transition induced porosity.

Scaffolds can have various dimensions which may depend on the particular use of the scaffold. A scaffold may have an average thickness of, for example, between 1 micron and 1 mm, between 10 microns and 0.5 mm, between 1 mm and 5 cm, between 1 mm and 1 cm, between 1 cm and 10 cm, or between 1 cm and 5 cm. Other thicknesses are also possible. The largest cross-sectional dimension of the scaffold can also vary from, for example, between 1 micron and 1 mm, between 10 microns and 0.5 mm, between 1 mm and 5 cm, between 1 mm and 1 cm, between 1 cm and 10 cm, between 1 cm and 5 cm, between 1 cm and 20 cm, or between 10 cm and 20 cm. A length of the scaffold can also vary from, for example, between 1 mm and 5 cm, between 1 cm and 10 cm, between 1 cm and 5 cm, between 1 cm and 20 cm, or between 10 cm and 20 cm. Other lengths are also possible. A scaffold may also have an aspect ratio (length to average cross sectional dimension) of at least 2:1, 3:1, 5:1, or 10:1 or more. It also should be appreciated that the size and thickness of a scaffold may vary along its length. In some embodiments, a scaffold may include a series of zones of different thicknesses (e.g., forming a series of rings that alternate between two different thicknesses).

Optionally, surface properties of a scaffold can be modified by various techniques. For example, in some cases, surfaces of a scaffold can be modified by coating and/or printing an additive proximate the structure. Surfaces may be modified with additives such as proteins and/or other suitable surface-modifying substances. For example, collagen, fibronectin, an RGD peptide, and/or other extracellular matrix (ECM) proteins or growth factors can be coated onto the scaffold, e.g., to elicit an appropriate biological response from cells, including cell attachment, migration, proliferation, differentiation, and gene expression. Cells can then be seeded onto surfaces of the scaffold. In one embodiment, cell adhesion proteins can be incorporated into certain portions of a scaffold to facilitate ingrowth of blood vessels. In another embodiment, growth factors can be incorporated into the scaffold to induce optimal cell growth conditions that triggers healthy tissue formation within certain regions of the scaffold. In other cases, additives can be incorporated into the material used to form the scaffold (e.g., embedded in the scaffold during fabrication).

In some cases, it may be desirable to modify all or portions of a scaffold with a material that inhibits cell adhesion, such as a surfactant (e.g., polyethylene glycol and polypropylene oxide-polyethylene oxide block copolymers). For instance, areas of a scaffold where it is not desirable for cellular growth can be coated with such materials, i.e., to prevent excessive soft connective tissue ingrowth into the structure from the surrounding tissue. In some cases, modification of surface properties of the scaffold can be used to position cells at specific sites on or within the scaffold. In some embodiments, a combination of cell-adhering and cell-inhibiting substances can be incorporated into various portions of a scaffold to simultaneously facilitate and inhibit cell growth, respectively.

In some embodiments, a scaffold can be coated with a porous material (e.g., a polymer such as a gel), e.g., prior to or during the seeding of cells. A porous polymer coating a scaffold can be used for a variety of purposes. For example, a porous polymer may be used to form pores on a scaffold that is otherwise non-porous. The porous polymer may allow, for example, sustained release of an active agent from the scaffold, e.g., to facilitate cell growth and/or cell adhesion as a function of time.

As described herein, cells may be seeded on various portions of a scaffold either before or after the scaffold is positioned in a bioreactor. In certain embodiments, cells may be seeded on at least one surface of a scaffold (e.g., a decellularized tissue construct) such that the cells are contained within a first or second chamber of a bioreactor. In certain embodiments, cells are seeded on both a first surface of the scaffold defining at least a portion of a wall of a first chamber and a second surface of the scaffold defining at least a portion of a wall of a second chamber. In certain such embodiments, the cells on the first surface are of the same type as the cells on the second surface and in other embodiments they are of different types. In certain embodiments, at least one of the cell types on at least one of the first and second surface is of a type normally associated with the type of tissue comprising a decellularized tissue construct in vivo.

As described herein, in some embodiments, aspects of the invention relate to growing cells to form cellular tissues, organ-like structures, and/or complete organs within the bioreactor. In some embodiments, the tissue or organ-like structures are grown to form of cavities surrounded by a cellular layer. In some embodiments, the tissue or organ-like structures are grown in the form of tubular structures. In some embodiments, the tubular structures may be airway structures (e.g., trachea, bronchi, bronchioles, or other airway passages), blood vessels (e.g., arteries, veins, vessels, capillaries), tubular portions of other organs (e.g., kidney, oesophagus, gut, stomach, intestine, colon, large intestine, small intestine, ducts, pancreatic duct, bile duct, gall bladder, bladder, urethra, urogenital structures, oronasal structures). It should be appreciated that tubular structures of the invention do not necessarily form perfect geometrical tubes. The shape of a tissue may be varied. In some embodiments, body cavities surrounded by a cellular layer may be created. For example, structures that mimic alveoli, heart cavities, kidney cavities, other organ or body cavities (e.g., ones that contain more or less actual tubular regions) may be grown or assembled according to aspects of the invention. It should be appreciated that the size of a tubular structure may be determined by the size of the support on which it is grown. Accordingly, the diameter and/or length may be determined by specifying the diameter and/or length of the acellular support (e.g., support matrix). Accordingly, a tubular tissue structure grown on the support may only represent a partial length of a tubular structure in a subject. For example, a length of airway or blood vessel grown in a bioreactor may be a portion of the length of the corresponding airway or blood vessel in a subject (e.g., in a human).

In some embodiments, a bioreactor is used to grow a tubular structure that corresponds to a tubular structure in the body. However, in some embodiments, a tubular structure grown on a bioreactor may be used to generate a sheet of tissue (e.g., skin, membrane, sheath, connective tissue, epithelial tissue, etc., or a combination thereof). For example, after growth the tubular structure may be cut or otherwise manipulated to generate a portion of tissue that can be used as a sheet of tissue, or to form a cellular sac or bladder (e.g., by cutting, shaping, and/or suturing one or more portions of tubular structure(s) grown on a bioreactor) or other cavity surrounded by cells.

Accordingly, in some embodiments, a tubular structure of the invention may be used to replace a corresponding body part (or a portion thereof) in a subject (e.g., a human patient). In some embodiments, an injured or disease tubular body structure, or an injured or diseased portion of a tubular body structure is replace surgically using a tissue grown in a bioreactor according to aspects of the invention.

In some embodiments, one or more tubular structures grown on a bioreactor may be used to form an artificial structure that can be used to replace a portion of an organ or tissue without specifically recreating or mimicking the actual body structure.

In some embodiments, one or more tubular structures grown on a bioreactor may be used in vitro to grow additional organ or organ structures (e.g., they may be used to seed cells for further organ growth).

In certain embodiments, additives can be added to a structure used or formed in a bioreactor, such as a tissue, an organ, or a scaffold. Additives may, for instance, increase a physical (e.g., strength) and/or chemical (e.g., hydrophilicity) property of the material, which can be advantageous during growth of the tissue or organ, or during or after being implanted into a patient.

Additives can be dispersed throughout the material of a structure (e.g., a scaffold), and/or can be incorporated within certain region(s) of a structure, for example by coating the scaffold or at least a portion of a tissue or organ through a gel or other layer. Additives can also be incorporated into and/or onto a structure by adsorption or by chemically reacting the additive onto a surface. Non-limiting examples of additives include bioactive agents (e.g., therapeutic agents, proteins and peptides, nucleic acids, polysaccharides, nucleic acids, and lipids, including anti-inflammatory compounds, antimicrobial compounds, anti-cancer compounds, antivirals, hormones, antioxidants, channel blockers, and vaccines), surfactants, imaging agents, and particles. If desired, additives may be processed into particles using spray drying, atomization, grinding, or other standard techniques. In some cases, additives can be formed into emulsifications, micro- or nano-particles, liposomes, or other particles that can be incorporated into the material of the structure.

In some cases, it is desirable to release an additive from portions of a structure when the structure is in its environment of use (e.g., implanted in a patient such as a mammalian body). Release of an additive may include hydrolysis and/or degradation of a portion of the structure. The release rate of the additive can be determined, in some instances, by the degradation rate of the material. The release rate of the additive can be controlled by the distribution of the additive throughout the material and/or by variation of the material microstructure (e.g., density of a polymer) such that the degradation rate varies with certain portions of the structure.

It should be appreciated that the cell types used to seed a bioreactor of the invention should be selected based on the type of tissue or organ structure that is being grown. In some embodiments, the cells may be epithelial, endothelial, mesothelial, connective tissue cells, fibroblasts, etc., or any combination thereof. In some embodiments, different cells may be used to seed the outer and inner surfaces of a tubular support structure (e.g., to form different inner and outer layers that correspond, at least in part, to natural inner and outer layers of a natural body structure). In some embodiments, only the inner or the outer surface of the support is seeded with cells.

It should be appreciated that components of the bioreactors described herein may be manufactured using metal, glass, rubber, plastic, composite, other natural or synthetic material, or any combination thereof. Where polymeric materials are used, such materials can be selected or formulated to have suitable physical/mechanical characteristics, for example, by tailoring the amounts of components of polymer blends, adjusting the degree of cross-linking (if any), etc. For instance, those of ordinary skill in the art can choose suitable polymers for use in bioreactors based on factors such as the polymer's compatibility with certain processing techniques, compatibility with any materials contained in the container (e.g., cells, nutrients, gases, etc.), compatibility with any treatments or pre-treatments (e.g., sterilization, autoclave), flexibility, puncture strength, tensile strength, liquid and gas permeabilities, and opacity.

Optionally, a vessel and/or bioreactor, or components thereof, may be transparent to certain wavelengths of light (e.g., to visible light, ultraviolet light, X-rays, etc.) to allow viewing and/or monitoring of contents inside the vessel. In certain embodiments, a vessel and/or bioreactor, or components thereof, is compatible with certain medical imaging techniques such as magnetic resonance imaging (MRI), fluoroscopy, computed tomography (CT), positron emission tomography (PET), thermography, ultrasound, etc. For instance, non-paramagnetic materials may be used for certain components when MRI is contemplated. Advantageously, such compatibility can allow detection of conditions or processes involving of cells, tissue(s), and/or organ(s) in the bioreactor, while maintaining sterility of the cells, tissue(s), and/or organ(s) contained in the bioreactor.

In some embodiments, a component is USP Class VI certified, e.g., silicone, polycarbonate, polyethylene, and polypropylene. Non-limiting examples of polymers that can be used to form component include polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. Components may comprise a substantially rigid material such as a rigid polymer (e.g., high density polyethylene), metal, and/or glass.

Bioreactors or components thereof may be sterilized using any suitable technique prior to use.

It should be appreciated that the examples described in the Figures and Examples relate to specific embodiments, and the related description is not-limiting to all embodiments described herein. However, it should be appreciated that structures, methods, compositions, devices, related components and technical steps and other aspects described in the context of the examples provided in the Figures and Examples can be used in combination with other embodiments and applications described herein.

The following examples are intended to illustrate certain embodiments of the present invention, but are not to be construed as limiting and do not exemplify the full scope of the invention.

EXAMPLES

Example 1

Bioreactor Considerations

In response to the need to replace pathological hollow organs, bioengineered products offer potential advantages over conventional treatments or allografts. Solutions using autologous cells, whether primary or stem cell-derived, offer functional restoration without the need for immunosuppression. Cells can be obtained from small biopsies, expanded and differentiated as necessary with high yield and purity. Starting with tissues such as skin, and moving onto more complex hollow organs including more than one cell type, such as bladder and trachea, tissue-engineered constructs, populated with autologous-derived cells, are showing promising results in early clinical trials. However, as structure and function becomes more complicated, the in vitro culture environment assumes an increasingly important role. It is necessary to address the diverse demands of more than one cell type, whilst increasing construct size raises serious questions about the ability of the environment to deliver adequate oxygen concentrations to all cells.

Bioreactors have been designed to provide solutions to a wide range of questions relating to cell and tissue engineering. Altering bioreactor microenvironments, adding control of medium flow and mixing, may guide structural and functional properties of tissues. Mechanical cues may be introduced to stimulate cells to produce specific components, or align cells in specific functionally relevant ways. As the goal of such research is to produce clinically useful products, bioreactors can also provide quality-assured and cost-effective manufacturing processes, with full compliance to relevant regulatory frameworks and the possibility of smooth scale-up/-out through automation and robotics. In this context, the present design and development provides a bioreactor for long tubular construct engineering that allows double seeding and culturing on both the inner and the outer surface of the matrix.

Thanks to the ultrastructure of biological acellular trachea matrices, two separate chambers are obtained inside and outside the tubular scaffold, and the two cell types can be fed with their proper culture medium. When using permeable porous scaffolds, one advantage of double seeding from both the inner and the outer surface of a matrix in a double-chamber bioreactor is that much better cell colonization can be achieved throughout the scaffold thickness, overcoming another generally limiting aspect of traditional static culture techniques. Moreover, the bioreactor rotates the construct around its longitudinal axis providing proper oxygenation to the three-dimensional structure and improves mass transport between the culture media and the adhering cells.

Gradients of oxygen and nutrients exist in engineered tissue, due to the balance between transport and rates of cellular consumption. Due to the difficulty of monitoring these gradients within tissue, predictive mathematical models have been developed for various bioreactor-cultured tissues, such as cardiac muscle, bone and cartilage. Oxygen is the focus of most of these models, due to its limited solubility in aqueous media. In this context, to further validate the bioreactor design, the feasibility of providing adequate oxygenation to cells within a thick scaffold was evaluated by using a mathematical transport model. This was used to predict oxygen concentration in the bioreactor-cultured trachea construct and in the culture media, as a function of construct geometry, thickness of cell invasion into the scaffold wall, cell densities and oxygen consumption rates. The model is designed to compare representative culture configurations and operating conditions of the rotating bioreactor. The consumption rates assumed here, 0.1 and 0.2 $\mu mol/10^6$ cells/h, were in the range for primary cells in culture, 0.1-0.5 $\mu mol/10^6$ cells/h. In the construct, the assumption that cells consumed oxygen uniformly at a zero-order rate was found to be an overestimate. Indeed, the model predictions demonstrated that oxygen concentrations do not fall to critical values at any time under a wide range of operating conditions. These data provide important validation of the rotating bioreactor as an adequate environment for the development of thick-walled, cellular, tissue-engineered hollow organ implants. Compared to certain derived finite element models, the analytical model was conceived in a parametric form, in order to single out critical bioreactor operating conditions, such as the culture of full-thickness cell-populated constructs at very high cell densities.

The trachea is an ideal model for early clinical translation of bioreactor-based tissue-engineering technology: it is a relatively simple conduit without intrinsic motility and there is a clear clinical need for large airway grafts. A clinically applicable tracheal substitute must meet numerous requirements: an external hyaline cartilage framework and an internal epithelial covering are essential. Although there are reports of small volumes of tracheal cartilage generation and clinical application, progress with long segment grafts has been limited by lack of an ideal scaffold, well-established epithelial and chondrocyte culture techniques, and an appropriate bioreactor environment.

Important considerations for a tracheal bioreactor include one or more of the following: (a) the provision of different culture conditions on either side of the organ wall, and (b) the need for adequate mass transport of gases and nutrients within a construct that has to be relatively long (e.g., more than 4 cm long) to be clinically useful. Based on these criteria, a stepwise work plan was developed consisting of the following: design of a bioreactor, development of predictive analytical models, in vitro testing, in vivo trials in animal model, application of human cells and performance of a first-time-in-human transplantation of the resultant recellularized construct.

Bioreactor Design

Objectives of the bioreactor design were: (1) to facilitate cell seeding procedures on both sides of a 3D tubular matrix, ensuring homogeneous plating; (2) to allow seeding and culturing of different cell types on either side of the tubular scaffold; (3) to enhance oxygenation of the culture medium and mass transport (oxygen, nutrients and catabolites) between the medium and the adhering cells; (4) to stimulate the cells with hydrodynamic stimuli, favoring the metabolic activity and the differentiation process; (5) to allow the achievement and maintenance of sterility and other criteria of Good Laboratory Practice (GLP), simplicity and convenience and (6) to permit the possibility of automation and scale-up/-out. Thus, a rotating double-chamber bioreactor was designed: the device allows confined seeding and culturing on both surfaces of a tubular matrix and includes rotatory movement of the scaffold around its longitudinal axis. By immersing half of the construct in media at any one moment, cells are cyclically exposed to gaseous (incubator atmosphere) and liquid (medium) phases. During exposure to the incubator atmosphere, the construct remains wet and the thin surface layers of culture medium are oxygen-saturated cyclically.

One embodiment of the device has three main components: culture chamber, motion and control units. A polymeric culture chamber houses the biologic sample and the medium for the whole culture period. Cylindrical scaffold holders were constructed with working ends from 10 to 25 mm in diameter—to house matrices of different dimensions—and a central portion of smaller diameter to expose the luminal surface of the matrix for seeding and culturing. Once the biological construct is in place, the inner space is confined (inner chamber) and isolated from the rest of the culture environment (outer chamber) by the graft wall. A co-axial conduit links the inner chamber to the external environment through an appropriate interface at the chamber wall which provides access to seed and feed the luminal surface of the construct. A luer-lock Hepa filter is connected to the conduit to preserve oxygenation and sterility. Secondary elements moving with the scaffold holder induce continuous mixing of the culture medium to increase its oxygenation and the exchange of nutrients and catabolites. The chamber is closed by a Petri-like cover to permit both oxygenation and sterility of the culture environment. The intact system can be autoclaved, significantly reducing contamination risks. The cell/matrix construct is moved by a DC motor (0-5 rpm adjustable) separated from the culture compartments. The connection between the motion unit and the culture chamber allows the first to remain in the incubator for the whole culture period, moving the chamber independently every time is needed (e.g., for sampling, medium exchange, etc.). An external control unit regulates and monitors rotation. At the end of the culture period, rotation is turned off, both chambers are emptied and refilled with fresh media and the bioreactor used to convey the graft to the operating theatre.

Accordingly, a novel bioreactor was designed to simultaneously address the requirements of seeding and culturing of different cell types on either side of a tubular matrix; nutrient supply and waste removal; biomechanical cues in the form of hydrodynamic shear stress; and autoclavability, ease of sterile handling, reliability, and precision compatible with good laboratory practice. The device rotated the airway construct around its longitudinal axis in culture medium tailored to the requirements of both cell-types, moving cells alternately between liquid (medium) and gaseous (air) phases (1·0-1·5 revolutions per min). A polysulphone chamber housed the medium and construct, which was rotated by a subsystem-controlled DC motor isolated from the culture chamber. Secondary elements induced continuous mixing of the culture medium to increase oxygenation, and the exchange of nutrients and catabolites to and from the adhering cells.

Oxygenation

Modeling predictions of oxygen profiles in the trachea tissue construct during rotating bioreactor culture were evaluated. Oxygen concentration in the tissue decreases for increasing colonization depth and density of cells. At a cell-colonized depth of 125 µm on both tissue sides, oxygen concentration is maintained above 0.18 mM (18.5% partial pressure or 138 mmHg) at all cell densities. At cell-colonized depths of 500 mm on both tissue sides, corresponding to a full-thickness cell invasion, oxygen concentration drops to a minimum level of 0.04 mM (4.1% partial pressure or 31 mmHg) at a cell density of $60 \times 10^6$ cells/cm$^3$, while zero concentration values are predicted in the internal regions of the construct at $80 \times 10^6$ cells/cm$^3$. Modeling predictions were made for the critical time in which a 95% drop in oxygen concentration is reached in the media filling the static bioreactor chambers. The critical time decreases for increasing cell-colonized depths and cell densities. Values range from around 4 h to 13 min and from 70 to 4 h, in the internal and external bioreactor chambers respectively.

A consideration was whether it would be theoretically feasible to support the oxygenation needs of a large, cellular organ construct within a rotating bioreactor. To explore this fundamental question, a mathematical model was developed and used to predict oxygen concentration profiles in tissue constructs of a clinically relevant thickness (1 mm), with varying oxygen consumption rate, colonization depth, and density of cells. Transport of oxygen in the construct was described by the mass conservation law in diffusion reaction $$\frac{\partial c}{\partial t} = D\nabla^2 c - V. \tag{1}$$

where c is the molar concentration, D is the diffusivity coefficient through the construct, V is the molar rate of consumption per unit volume. The following assumptions were made. The profiles were calculated in stationary state. A cylindrical symmetry was assumed, using the hypothesis of infinite length, such that one-dimensional profiles were calculated within the construct thickness. The tissue thickness was modeled in three distinct regions (FIG. 2B): region 1, facing the inner bioreactor chamber, populated with epithelial cells, region 3 facing the outer bioreactor chamber, populated with chondrocytes, and region 2, acellular, in between. Rates of oxygen consumption, V, were determined as the product of maximal mammalian cells consumption rate, Vmax, and cell volume density, Nv $$V = V_{max} \cdot N_V. \tag{2}$$

The following boundary conditions were assumed. The axial rotation allows both internal and external construct surfaces to remain in contact with oxygen-saturated films of medium. Thus, the liquid-phase oxygen concentration at the construct surfaces was assigned the value of the equilibrium concentration for oxygen in the media, calculated using Henry's law constant for $O_2$ in water at 37° C. (Table 1). The concentration profiles and the oxygen fluxes were assumed to be continuous at all interfaces between regions.

$$c(r) = c_1 + \frac{V_1}{4D}(r^2 - R_1^2) + a \qquad (3)$$

$$c(r) = c_1 + \frac{V_1}{4D}(R_2^2 - R_1^2) + \frac{V_1 R_2^2}{2D}\ln\frac{r}{R_2} + a \qquad (4)$$

$$c(r) = c_4 + \frac{V_2}{4D}(r^2 - R_4^2) + \frac{1}{2D}\ln\frac{r}{R_4}(V_1 R_2^2 - V_2 R_3^2) + a \qquad (5)$$

for $R_1 < r < R_2$, $R_2 < r < R_3$, and $R_3 < r < R_4$, respectively, where $$a = \frac{\ln\frac{r}{K_1}}{\ln\frac{K_1}{K_1}}\left\{c_4 - c_1 + \frac{1}{2D}\left[\begin{array}{c}V_1 R_2^2 \ln\frac{R_2}{R_4} + V_2 R_3^2 \ln\frac{R_4}{R_3} + \\ \frac{V_2}{2}(R_3^2 - R_4^2) + \frac{V_1}{2}(R_1^2 - R_2^2)\end{array}\right]\right\}. \qquad (6)$$

The parameter values used in the calculations are given in Table 1. To determine the effect of specific parameters on the profiles, the parameters were varied and the profiles recalculated. To evaluate the effect of cell invasion, the two regions populated with cells were assumed of three thickness values, equal on both cell-populated regions: 125, 250 and 500 μm. For each thickness value, the oxygen profile was calculated at four values of increasing cell volume density: $20 \times 10^6$, $40 \times 10^6$, $60 \times 10^6$ and $80 \times 10^6$ cells/mL.

A second mathematical model was implemented and used to predict oxygen concentration drop in the culture media during those periods when the bioreactor rotation is turned off (for example during construct transfer to the surgical room). Again, transport of oxygen was described by the mass conservation law in diffusion reaction (Eq. (1)), with new assumptions and boundary conditions.

The diffusion term was neglected, in the hypothesis of well mixed medium. Michaelis-Menten kinetics was assumed for the uptake of oxygen by cells, V $$\frac{dc}{dt} = -V(c) = -V\frac{c}{K_m + c} \qquad (7)$$

where $K_m$ is the Michaelis-Menten constant. Oxygen uptake was assumed to be linear at very low concentrations and it was expressed in total moles $$\frac{dc}{dt} \cdot V_m = -V \cdot \frac{c}{K_m} \cdot V_t \qquad (8)$$

where $V_m$ and $V_t$ are the chamber priming volume and the tissue volume, respectively. For both chambers, the initial condition assumed was 20% oxygen partial pressure and the final condition was a critical 1% partial pressure. Solving Eq. (8) yielded the expression of the time, $t_{cr}$, in which the critical oxygen concentration is reached $$t_a = \left(-\frac{K_m \cdot V_m}{V \cdot V_t}\right) \cdot \ln 0.05. \qquad (9)$$

The parameter values assumed for calculation of $t_{cr}$ are given in Table 1. To determine the effect of specific parameters on $t_{cr}$, the parameters were varied and the critical times recalculated, as described above for the oxygen profiles.

Bioreactor Cultivation of the Trachea Construct

Both cell seeding onto the scaffold and cellularized construct dynamic culture were performed inside the bioreactor, avoiding construct manipulation between the two operations and thus limiting the risk of cell construct contamination. The

TABLE 1

Model parameters used to predict oxygen concentration profiles in a trachea tissue construct cultured in a double-chamber rotating bioreactor, and to predict oxygen concentration in the culture media filling the chambers with bioreactor rotation turned off.

| Parameter | Inner | Outer |
|---|---|---|
| $O_2$ solubility in water at 37° C. [nmol/mL/mmHg] | 1.3 [15] | |
| Tissue construct wall thickness, $R_4 - R_1$ [mm] | 1 | |
| $O_2$ diffusion coefficient in $H_2O$ at 37° C., D [cm$^2$/s] | $2.1 \times 10^{-5}$ [15] | |
| $O_2$ consumption rate, $V_{max}$ [μmol/$10^6$ cells/h] | 0.2027 [16] | 0.108 [17] |
| Boundary $O_2$ concentration in culture [mM] | 0.195 | 0.195 |
| Boundary $O_2$ concentration post-implant [mM] | 0.195 | 0.05 |
| Thickness of the cell-populated region [μm] | 30 (validation culture), 125, 250, 500 (parametric study) | |
| Construct cell volume density, $N_v$ [$10^6$ cells/mL] | 20, 40, 60, 80 (parametric study) | |
| Construct cell volume density, $N_v$ [$10^6$ cells/mL] | 41.25 (validation culture) | 61.33 (validation culture) |
| Chamber priming volume, $V_m$ [mL] | 10 | 120 |
| Michaelis-Menten constant, $K_m$ [mM] | 0.15 [18] | | acellular matrix was positioned onto the cylindrical holder, fixed at both ends with surgical sutures to ensure rotation and positioned inside the bioreactor. The recipient's cultured cells were detached from culture flasks, diluted with medium ($1 \times 10^6$ cells per mL), and seeded onto the matrix. Chondrocytes were dropped longitudinally on the external surface of the matrix with a microsyringe, while epithelial cells were injected onto the internal surface. After completion of the seeding process, each chamber was filled up with its respective complete media to totally submerge the seeded matrix. The resultant cellularized construct was maintained in static conditions for 24 h to promote cell adhesion (37° C., 5% $CO_2$). Media volumes were then reduced so that nearly half of the matrix was exposed to the incubator atmosphere (75 mL external, 4 mL internal) and dynamic culture was started at 1.5 revolutions per min (37° C., 5% $CO_2$) for 72 h. The external medium (chondrocytes) was changed every 48 h and the internal medium (epithelial cells) every 24 h. At the end of the culture period, the bioreactor rotation was turned off, both chambers were emptied and completely refilled with fresh media and the bioreactor was delivered to the operating room. The graft was then cut to shape and implanted into the patient as a replacement for her left main bronchus. Ethical permission was obtained from the Spanish Transplantation Authority and the Ethics Committee of the Hospital Clinic, Barcelona.

Predictions of the concentration profile within the tissue construct were obtained from Eqs. (3) to (6), in two conditions: during bioreactor culture and post-implantation. The parameter values used for all calculations relevant to bioreactor validation are gathered in Table 1. In both conditions, the thickness of both the cell-populated regions was assumed equal to 30 mm, based on measurements taken on histological sections of the construct. In the implanted condition, at the construct inner surface oxygen was set at 20% partial pressure whereas at the construct outer surface it was assigned a 5% partial pressure value, corresponding to venous blood oxygen tension, 38 mmHg. The critical time in which oxygen partial pressure in the medium drops to 1% in the absence of bioreactor rotation, tcr, was calculated for both chambers using Eq. (9).

Major challenges in functional airway bioengineering are uniform and highly efficient cell seeding on both the outer and inner surface of the three-dimensional tubular matrix, co-culturing different cell types, and optimum mass transport between the culture medium and the growing tissues. To address these issues, a novel bioreactor suitable for in-vitro engineering of long airway grafts was developed. Early on, it was realized that the two types of cells used here required different culture conditions. Therefore, the prototype bioreactor created for preclinical work was designed to provide two separate sterile compartments, each with a rotating air-medium interface. Viability of cells in both compartments was maintained to the point of operation. The dynamic culture environment in the bioreactor, controllable and reproducible, is important for the nutrient supply and waste removal needed to sustain large three-dimensional constructs. The rotation provides the hydrodynamic shear stress necessary to promote metabolic activity and proper differentiation of the seeded cells.

Example 2

Cells and Matrix

Bone Marrow Stem Cell (BMSC) Culture and Characterization

BMSCs were isolated and cultured. Plastic-adherent mesenchymal BMSCs were expanded until 90% confluent, in the presence of 5 ng/mL basic fibroblast growth factor (PeproTech, London, UK), before being passaged and re-plated at $1 \times 10^6$ cells per 175 $cm^2$ flask.

Prior to differentiation and subsequent implantation into the patient, the stem cell characteristics and differentiation potential of the BMSC population were assessed. Phenotypic cell surface markers present on passage 3 cells were analyzed by fluorescence-activated cell sorting (FACS). Positive expression was defined as the level of fluorescence greater than 98% of the isotype control.

Having verified the stem cell characteristics of the BMSC population, passage 3 cells were induced to differentiate into chondrocytes, prior to seeding onto the decellularized donor scaffold using the bioreactor.

Respiratory Epithelial Cells Culture

Respiratory epithelial cells were isolated and cultured. Briefly, bronchoscopic biopsy samples were placed in 70% ethanol for 30 s and then in a solution containing 0.25% trypsin (Sigma-Aldrich), 100 U/mL penicillin and 100 mg/mL streptomycin in PBS in a centrifuge tube overnight at 4° C. At 24 h, the tissue was warmed to 37° C. for 45 min and then disrupted by repeated vigorous pipetting with a plugged glass Pasteur pipette. The trypsin solution was neutralized with complete medium (Dulbecco's modified Eagle's medium [DMEM], Invitrogen, Paisley, UK), containing 10% fetal calf serum (PAA, Yeovil, UK), penicillin (100 U/mL), and streptomycin (100 µg/mL). The dissociation process was repeated, and the cell suspension was centrifuged at 1000 revolutions per min for 10 min. The cell pellet was resuspended in keratinocyte serum-free medium (Invitrogen), supplemented with 25 µg/mL bovine pituitary extract, 0.4 ng/mL recombinant epidermal growth factor, 0.06 mmol/L calcium chloride, 100 U/mL penicillin and 100 µg/mL streptomycin, the cells were seeded in a final volume of 5 mL in 25 $cm^2$ flasks, and the cultures were incubated at 37° C., 5% $CO_2$ for 2-3 days for adherence. Culture medium was then replaced every 5 days. Cytospins of cultured autologous recipient epithelial cells at first passage were subjected to three-color immunofluorescence histology for cytokeratins 5 and 8, type I collagen and counterstained with DAPI to confirm epithelial phenotype before attachment to the matrix in the bioreactor. Ten fields of view were examined per slide, equating to a minimum of 250 cells.

Human Tracheal Decellularization

A 7 cm tracheal segment was retrieved from a transplant donor and rinsed in phosphate buffered saline (PBS) containing 1% penicillin, 1% streptomycin, and 1% amphotericin B (all Sigma, Barcelona, Spain), having removed all loose connective tissue. 25 cycles of the decellularization protocol were applied: tissue was extensively washed with distilled water for 72 h, then incubated in 4% sodium deoxycholate and 2000 kU deoxyribonuclease I in 1 mmol/L sodium chloride (Sigma Chemicals, Barcelona, Spain). The presence of cellular elements and MHC-positive cells was verified by immunohistochemistry after each cycle. Primary anti-human HLA-D (BD Biosciences, Oxford, UK) and HLA-ABC (Abcam, Cambridge, UK), secondary antibodies (Vectastain ABC kit, Vector Laboratories), and a peroxidase substrate kit (DAB, Vector Laboratories) were used to detect MHC antigen expression. For negative controls, the primary antibody was omitted. Paraffin-embedded sections of the matrix were also stained with 4-6-diamidino-2phenylindole (DAPI, Vector Laboratories, Burlingame, Calif., USA) to detect residual nuclei inside the treated tissue. Samples of the treated matrix were fixed with 3% glutaraldehyde (Merk, Darmstadt, Germany) in 0.1 M cacodylate buffer (Prolabo, Paris, France), subjected to critical point drying and gold sputtering, and examined by scanning electron microscope (JSM6490, JEOL, Japan).

Characterisation of BMSC Population

BMSCs were isolated from an autologous bone marrow aspirate by their ability to adhere to tissue culture plastic. The cells were allowed to proliferate until a sufficient number were obtained for seeding onto the decellularized donor trachea. Prior to seeding, passage 3 BMSCs were characterized to assess the quality of the stem cell preparation.

FACS analysis was used to assess the population for phenotypic cell surface markers associated with multipotent stem cells. In agreement with certain published results, the population was positive for CD105 (99.3%), STRO-1 (30.5%), VCAM-1A (28.3%), CD49a (25.8%), bone morphogenetic protein receptor 1A (1.9%) and CD117 (1.3%). As expected the cells were negative for CD34, a hematopoietic stem cell marker. The multi-lineage differentiation potential of the BMSCs was assessed by examining their chondrogenic, osteogenic and adipogenic capacities. The BMSC population was successfully differentiated into both osteoblasts, resulting in cultures rich in minerals, and adipocytes, as shown by the presence of fat vacuoles stained with oil red-O. In addition, a white, shiny tissue resembling hyaline cartilage at the macroscopic level was generated when BMSCs were seeded onto PGA scaffolds and cultured in chondrogenic differentiation medium for 35 days. When duplicate tissue-engineered cartilage constructs were analyzed for several matrix proteins, amounts of proteoglycan and type II collagen, the two major constituents of adult hyaline cartilage, were similar to certain published results. Levels of type I collagen, which is virtually absent in normal, mature hyaline cartilage, were minimal.

Having shown that the BMSC population displayed cell surface marker and multipotential characteristics of stem cells, passage 3 cells were induced to differentiate into chondrocytes by stimulating with TGF-b3, dexamethasone and insulin in the presence of para-thyroid hormone-related peptide to inhibit hypertrophy. The cells were then seeded onto the outer surface of the decellularized donor trachea using the bioreactor.

Respiratory Epithelial Cells Culture

All cells in epithelial culture stained positive for cytokeratins 5 and 8 immediately before seeding and had epithelial morphology on light microscopy of cultured cells. Fibroblasts were not detected morphologically or by immunofluorescence histology looking for cells positive for type I collagen. As at least 250 cells were examined per slide, this represents greater than 99.6% purity of the epithelial cell culture.

Human Trachea Decellularization and Preparation of an Airway Matrix

After 25 cycles of decellularization, epithelial and glandular cells were completely removed from the tracheal matrix, while only a few chondrocytes were still visible. Treated tissue was free from HLA-A, HLA-B, and HLA-C antigens, although low amounts of focal MHC class II expression were still seen in a few areas. High magnification of the luminal surface revealed that the basal lamina was partially maintained. Indeed, an alternation of smooth areas and matrix fibers was well visible. The external side of tracheal matrix was characterized by bundles of fibers irregularly arranged.

A 7 cm tracheal segment was retrieved from a 51-year-old white female transplant donor who had died of cerebral haemorrhage (blood type O, and negative viral, treponemal, and β-human chorionic gonadotropin serology). All loose connective tissue was removed, and the trachea rinsed in phosphate buffered saline (PBS) containing 1% penicillin, 1% streptomycin, and 1% amphotericin B (all Sigma, Barcelona, Spain). Twenty five cycles of the decellularization protocol were applied over 6 weeks, with the following modifications. Briefly, tissue was stored in distilled water for 72 h, then incubated in 4% sodium deoxycholate and 2000 kU deoxyribonuclease I in 1 mmol/L sodium chloride (Sigma Chemicals, Barcelona, Spain). The presence of cellular elements and MHC-positive cells were verified histologically after each cycle. After the periodic removal of sections for histology, a final graft length of 6·5 cm was obtained, which was reduced to 5 cm intraoperatively to fit the defect.

With the detergent enzymatic method, tracheal cells were progressively removed. After 25 cycles of decellularization, the epithelial and glandular cells were removed. The few visible chondrocytes were distorted and mostly anuclear. However, treated trachea retained the same architecture as native controls. 25 cycles were needed to completely remove HLA-A, HLA-B, and HLA-C antigen expression, although low amounts of focal MHC class II expression were still seen in a few areas.

With this protocol HLA antigens were removed from a donor matrix, which was then readily colonized by the recipient's epithelial cells and chondrogenic mesenchymal stem cells. This matrix was used to prepare and transplant an airway graft for a patient with left main bronchus malacia, resulting in a patent airway and an improved quality of life. By contrast with solid organ transplants, which take place in sterile mesenchymal environments, the airway represents an interface between internal and external environment. Unsurprisingly, the airway mucosa has immunologically active cells playing a key part in airway transplantation, and these contribute to acute allograft rejection, which requires high-dose immunosuppression. Unlike other transplants, airway replacement is rarely a life-saving procedure, so a completely non-immunogenic tracheal allograft with preserved functional and mechanical characteristics is the minimum target for organ replacement.

The extracellular matrix plays an active part in regulating diverse aspects of cell biology that are essential to the normal function of tissues. Therefore, recent bioengineering studies have focused on the application of extracellular matrix-derived prosthetic materials as bioactive supports. Scaffolds derived from decellularized tissues have been shown to support in-vitro adhesion, growth, and function of several cell types, and have been used successfully in animals and man, and act as a template for ingrowth and remodeling.

Histology, Immunohistology, and Immunofluorescence Histology of Matrices

To quantify the remaining cells after each detergent enzymatic cycle, ten representative 5 μm paraffin-embedded sections of the matrix with 4'-6-diamidino-2-phenylindole were stained (DAPI, Vector Laboratories, Burlingame, Calif., USA), and counted the total number of nuclei with fluorescence microscopy (mean nuclear count×$10^5$ per $\mu m^2$ [SD]). For morphological assessment, adjacent, paraffin-embedded sections with haematoxylin and eosin (both Merck, Darmstadt, Germany) were stained. MHC antigen expression in human tissue by use of primary anti-human HLA-DR, HLA-DP, HLA-DQ antibodies (all three BD Biosciences, Oxford, UK) and HLA-ABC antibodies (Abcam, Cambridge, UK), secondary antibodies (Vectastain ABC kit, Vector Laboratories), and then a peroxidase substrate kit (DAB, Vector Laboratories) were measured. For negative controls, the primary antibody was omitted.

Cellular brushings from the external surface of the seeded matrix preimplantation and from the graft lumen 4 days postoperatively to triple-color immunofluorescence were subjected with a mouse anti-human monoclonal antibody to collagen II (Abcam) to confirm the presence of chondrocytes, an anti-human monoclonal antibody to cytokeratins 5 and 8 (BD Biosciences) to identify epithelial cells, and stained for nuclear DNA with DAPI.

Preparation of Recipient's Autologous Epithelial Cells

Bronchoscopic biopsy samples of the right main bronchial mucosa and rhinoscopic biopsy samples of the right inferior turbinate mucosa were taken from the recipient under local anaesthesia and sedation, and were placed in PBS at 4° C. Since bronchial epithelial cells grew far more readily than did nasal cells, only the bronchial cells were used subsequently for graft development.

Biopsy samples were transported in ice-cold PBS containing penicillin (100 U/mL) and streptomycin (100 μg/mL) (both Sigma-Aldrich, Dorset, UK). Samples were placed in 70% ethanol for 30 s and then in a solution containing 5 mL 1% trypsin (Sigma-Aldrich), 15 mL PBS, and 800 μL penicillin and streptomycin in a centrifuge tube overnight at 4° C. At 24 h, the tissue was warmed to 37° C. for 45 min and then disrupted it by repeated vigorous pipetting with a plugged glass pasteur pipette. The trypsin solution was neutralized with complete medium (Dulbecco's modified Eagle medium [DMEM], Invitrogen, Paisley, UK), containing 10% fetal calf serum (PAA, Yeovil, UK), penicillin (100 U/mL), and streptomycin (100 µg/mL). The dissociation process was repeated, and the cell suspension was centrifuged at 1000 revolutions per min for 10 min. The cell pellet was resuspended in complete DMEM, the cells were seeded in a final volume of 5 mL in 25 cm$^2$ flasks, and incubated the cultures at 37° C., 5% $CO_2$ for 2-3 days for adherence. The culture medium was then changed to keratinocyte serum-free medium (Invitrogen), supplemented with 25 µg/mL bovine pituitary extract, 0.4 ng/mL recombinant epidermal growth factor, and 0.03 mmol/L calcium chloride. The culture medium was changed every 5 days.

Cytospins of cultured autologous recipient epithelial cells were subjected at first passage to dual-color immunofluorescence histology for cytokeratins 5 and 8 as above, counterstained with DAPI to confirm epithelial phenotype before attachment to the matrix in the bioreactor. All cells in epithelial culture stained positive for cytokeratins immediately before seeding, and any fibroblasts were not detected morphologically and immunohistologically.

Preparation of Recipient's Autologous Chondrocytes

To prepare the chondrocytes, 10 mL volume of bone-marrow aspirate, taken on the day of culture, was added to 40 mL of complete medium (DMEM, containing 1000 mg L-glucose, Sigma-Aldrich), 10% fetal bovine serum (Autogen Bioclear, Wilts, UK), 100 U/mL penicillin, 100 µg/mL streptomycin, and 2 mmol/L GlutaMax-I (Invitrogen) in a centrifuge tube. After centrifugation of the cells for 5 min at 600 g, the fat layer and supernatant was removed, and the cell pellet was resuspended containing mesenchymal stem cells in 20 mL of complete medium. Cells were counted and seeded in 175 cm$^2$ vented flasks at a density of $1.1 \times 10^6$ per mL with 5 ng/mL basic fibroblast growth factor (PeproTech, London, UK). Cells were incubated undisturbed at 37° C. in a humidified 5% $CO_2$ atmosphere for 72 h for promotion of adherence, and the medium was replaced with fresh complete medium containing basic fibroblast growth factor every 3 days. When cells reached 90% confluence, the medium was removed and the cells were washed once with Hanks' balanced salt solution and then passaged with 0.25% trypsin-EDTA (edetic acid, Invitrogen). At each passage, the cells were seeded at a density of $1 \times 10^6$ per mL. To induce chondrocyte differentiation, the culture medium was changed to complete medium containing 10 ng/mL of recombinant human transforming growth factor-β 3 (R&D Systems, Abingdon, UK), 10 nmol/L recombinant parathyroid hormone-related peptide (PeproTech), 100 nmol/L dexamethasone, and 10 µg/mL insulin (both Sigma-Aldrich, Dorset, UK), and the cells incubated for 72 h. No fibroblasts could be detected in the chondrocyte culture before seeding.

Example 3

Seeding of Cells

The recipient's cultured cells were seeded onto the matrix within the bioreactor. The chondrocytes were detached from culture flasks, diluted with medium ($1 \times 10^6$ cells per mL), and applied longitudinally to the external surface of the matrix with a microsyringe. Concurrently, the internal surface was seeded with the same density of epithelial cells through a separate access of the holding cylinder. Every 30 min, the matrix was rotated 90 degrees until all surfaces had been completely exposed to cells. Cell medium was added (75 mL externally, 4 mL internally) and rotation started at 1·5 revolutions per min (37° C., 5% $CO_2$). The external medium (chondrocytes) was changed every 48 h and internal medium (epithelial cells) every 24 h, and the extracted medium was tested for microbial colonisation. The total period of bioreactor culture was 96 h.

Bioreactor Cultivation of the Trachea Construct

The procedure described to seed chondrogenic BMSCs and epithelial cells on either side of a long tubular tracheal matrix allowed easy and highly efficient cell seeding. The bioreactor worked properly and no contamination was observed during the whole culture period. Autoclavability, ease of handling under sterile conditions, reliability and precision ensured full compatibility of the device with the GLP rules.

Modeling predictions of oxygen profiles in the tracheal tissue construct during rotating bioreactor culture and post-implantation were used. Oxygen in the tissue is maintained at 20% partial pressure during culture and ranges linearly from 20% to 5% partial pressure (38 mmHg) after implantation. The critical time in which a 95% oxygen drop is reached in the media filling the static bioreactor chambers was around 7 h for the inner chamber and 83 h for the outer chamber. Therefore, a maximum time of 7 h was available to safely deliver the construct to the operating room and maintain it in static conditions until the time of implant.

Immediately prior to implantation, the internal surface of the graft was brushed, and again by bronchoscopy at two weeks. At two months, biopsies of the graft wall were taken by flexible bronchoscopy under topical anaesthesia and sedation. Specimens were embedded in OCT (Sakura, Calif.), snap-frozen and mounted on cork disks in isopentane cooled over liquid nitrogen, and stored at −80° C. Five micrometer frozen tissue sections were cut on a cryostat (Bright, Huntingdon) and processed for haematoxylin and eosin histology and multiple color immunofluorescence. Sections were air dried and fixed for 10 min in ice-cold acetone before blocking for 1 h with 5% human and goat serum. Samples were then incubated at 4° C. overnight with optimally titrated primary monoclonal antibodies in two combinations. Stain 1 consisted of mouse anti-human monoclonal antibody to collagen II (Abcam) to confirm the presence of chondrocytes, an anti-human monoclonal antibody to cytokeratins 5 and 8 (BD Biosciences) to identify epithelial cells, and stained for nuclear DNA with DAPI. Stain 2 used the same antibody to cytokeratins 5 and 8 (BD Biosciences) plus an anti-human HLA-DR, DP, DQ (PharMingen) to identify MHC class II positive cells (antigen-presenting cells and vascular endothelium). Sections were washed in PBS and incubated for 1 h at room temperature with goat anti-mouse isotype-specific secondary fluorochrome conjugates (Southern Biotechnology Associates Inc, USA). Where necessary, a three-stage procedure used biotinylated isotype-specific secondary antibodies followed by AMCA Avidin D (Vector Laboratories Inc, USA). Sections were mounted with Vectashield® (Vector laboratories Inc, USA) and sealed with nail varnish. Multiple fields at 20× magnification were digitized and grey scale images captured on a Leica DMRA microscope using a Hamamatsu Orca-ER camera and Q-Fluoro software (Leica, UK).

Example 4

Graft Implantation

After general anaesthesia and double-lumen endotracheal intubation, a left posterolateral thoracotomy (fifth intercostal space) was performed and the distal trachea, left main bronchus, and the left recurrent and phrenic nerves of the recipient were carefully dissected and fully mobilised. The left main bronchus was resected, recreating its take-off on the lateral aspect of the distal trachea via a 2 cm×2 cm orifice, and preserving distally the upper lobe take-off and the lobar carina. The graft was cut to shape, and anastomosed end-to-end proximally and distally. Fitting to the two lumens of different sizes was helped by the retained elasticity of the trachealis segment of the graft. Bilateral ventilation was restored and the recipient's left lung immediately ventilated well. After checking for leaks, the chest was closed, and the patient was extubated. The recipient was monitored for 2 days in the intensive care unit, when she was well enough to return to a general ward and was discharged on the tenth postoperative day. Ethical permission was obtained from the Spanish Transplantation Authority and the Ethics Committee of the Hospital Clinic, Barcelona.

Postoperative Care and Monitoring

The postoperative course was uneventful. The recipient underwent rigid bronchoscopy at 4 days, and bronchoscopy and serological testing at 14 days, 1 month, and 2 months. Adjacent microvascular recordings were taken by use of a dedicated laser-doppler probe (moorLAB, Moor Instruments, Axminster, UK). Brushings were taken at 4 days and cytospins were prepared.

Anti-HLA Antibody Serology

Recipient anti-donor HLA antibody production was screened and specificity tested using the National Institutes of Health version of the complement-dependent cytotoxic test, against a panel of 64 cell lines and by solid-phase antigen test FlowPRA class I and class II screening beads (One Lambda, Canoga Park, Calif., USA). Solid-phase flow cytometry was used for confirmation of antibody production and specificity. Tests were done preoperatively, and at 14 days, 1 month, and 2 months postoperatively.

The recipient had no complications from the operation and was discharged from hospital on the tenth post operative day. She has remained well since, and is able to walk up two flights of stairs, walk 500 m without stopping, and care for her children. Lung-function tests done at 2 months were all within the normal range for age and sex. Serological examination showed the complete absence of anti-donor HLA antibodies at 14 days, 1 month, and 2 months.

At 4 days, the graft was almost indistinguishable from adjacent normal bronchial mucosa. Laser-doppler readings confirmed a rich adjacent microvascular bed. At 14 days, there was an adherent layer of mucus on the graft surface in which no inflammatory cells were detected cytologically. At 14 days, 1 month, 2 months, and 3 months, the graft seemed healthy with a strong laser-doppler recording (at 2 months: 6·0 mL per min for graft, 5·8 mL per min for right bronchus). At 1 month, the appearance of the graft was indistinguishable from native trachea, and local mucosal bleeding was elicited when the biopsy sample was taken, indicating successful revascularization. Three-dimensional CT-reconstructions preoperatively and at 1 month postoperatively showed a transformation in the appearance of the airway from near-total collapse to wide patency.

Cytological analysis of the luminal surface at 4 days showed plentiful epithelial cells that were phenotypically identical to those in culture before seeding. Viable chondrocytes were also seen in these brushings. Similar cytospins were prepared from the external surface of the graft before implantation, and both cell types were found to be present.

A major potential problem with bioengineered organs is the provision of a functional blood supply. In this study, laser-doppler measurements showed a healthy, adjacent microvascular bed from postoperative day 4 and active mucosal bleeding at 30 days. Although not studied, angiogenic cytokines (basic fibroblast growth factor, transforming growth factor β) might be present within decellularized matrices, and could contribute to timely revascularization. In support of this view, when sections of detergent enzymatic method-treated pig trachea were implanted into a Balb/c mouse dorsal skin pouch, graft neovascularization was seen by 2 weeks.

25 cycles of detergent enzymatic method completely removed cell membranes, all MHC class I and virtually all MHC class II expressions, but retained some other cellular elements in cartilaginous areas. On the basis of results obtained with other engineered tissues, the retained elements could provide helpful signals to both graft and host cells, and might reduce the inflammatory response. Conversely, the possibility is that cellular residues could express minor antigens capable of inducing a chronic rejection response. However, minor antigens play a restricted part in clinical transplantation and here there was no sign of inflammation or anti-donor antibodies at 2 months.

Although it has been previously described how nasal epithelial cells can be cultured for tissue-engineering purposes, in this study, they grew so fast, that apoptosis occurred in earlier passages than with bronchial cells. However, with a reduced detergent enzymatic method time, nasal cells might be preferred for future airway tissue-engineering applications. Although the graft was completely covered with viable mucosa at 1 month, it is not certain whether these cells originated from those seeded or whether they grew in from an adjacent healthy airway. Although animal studies have provided circumstantial evidence that the implanted cells are likely to contribute in an important way, further research into the fate of these cells is essential before embarking on full clinical trials with the present protocol.

In vitro, epithelial cells and chondrocytes became deeply embedded within the matrix by 24 h. This finding suggests that the matrix is highly permissive and an ideal immediate environment for these cells. In fact, after 24 h in the bioreactor, no cells (alive or dead) could be detected in the culture medium, suggesting a near 100% adherence. The presence of clearly viable epithelial cells and chondrocytes on the graft surface at 4 days confirms this view, and shows that the cells continue to function in vivo. Both types of cells could be seen in cytological samples from both surfaces of the conduit, despite clear structural separation of the two bioreactor compartments. One interpretation is that cells were free to migrate through the full width of the graft within a short space of time. If confirmed, this interpretation is important, with implications for future tissue-engineering designs. It has been shown in animals that an ordered architectural association between different cell types is not necessary for functional healing. The present findings extend this observation to humans.

It is preferable to minimize trauma to both the patient and the graft, and so cellular analysis was restricted to the cytology before and 4 days postimplantation, at which times bronchoscopy was clinically indicated in any case. Since heterotopic-pig experiments showed some success with decellularized grafts in the absence of recolonization with autologous cells, the contribution of autologous cells is not certain, and the formal possibility remains that the addition of cells is, in fact, not necessary. However, the rapid integration seen in this study is consistent with animal models in which cells seem to play a crucial part.

Despite the larger number of detergent-enzymatic method cycles used in the clinical setting than that used in preclinical work, and the known structural differences between pig and human trachea, the similarity to native trachea in terms of tissue handling and elasticity, both preoperatively and postoperatively, was remarkable and commensurate with the biomechanical results of preclinical studies. The elasticity of the trachealis segment in particular allows adjustment of lumen size to the recipient's bronchus A significant aspect of these studies is based, in part, on the fact that the bioreactor made it possible to properly repersonalize a donor trachea and to successfully perform the first engineered airway transplantation without the need of any immunosuppressive therapies. The graft is still functioning well and there is no sign of rejection at one year post-implantation. Cytological and histological studies were necessarily limited by the need to avoid trauma to the graft. However, vigorous angiogenesis was confirmed by laser Doppler recordings from two weeks, and at biopsy at two months.

The persistence of viable chondrocytes, and a layer of viable epithelial cells at two months post-surgery also were confirmed. However, the epithelial layer, whilst macroscopically intact and clearing mucus by this time, was microscopically discontinuous. Thus, further work to improve epithelial cell coverage of the internal surface of the graft pre-operatively is necessary, and this is an important design consideration for further refinements of the bioreactor. Furthermore, the application of flow stimuli to the internal compartment of the bioreactor is believed to encourage appropriate alignment and function of cilia prior to implantation, thereby initiating appropriate clearance of mucus from the first post-operative day.

Accordingly, following mathematical modeling of hypothetical cellular oxygen requirements, a double-chamber bioreactor was designed to support hollow organ (tracheal) recellularized implants. It was confirmed that the bioreactor configuration allowed oxygenation to be maintained despite the thickness of the implant wall, and that two autologous cell types with disparate media requirements could be supported, expanded and would migrate effectively on the scaffold. Ultimate validation of the bioreactor's effectiveness was provided by its central role in the first stem cell-derived, tissue-engineered organ, which continues to function well ten months post-implantation. Further refinements will be necessary to permit scale-up and full clinical trials, as well to explore hypothetical ways of improving graft production, such as encouraging angiogenesis and orientated ciliary function.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A bioreactor, comprising:
   a vessel;
   a cylindrical scaffold defining an outer wall of an inner chamber and an inner wall of an outer chamber, wherein the scaffold is removably positioned within the vessel and configured to rotate relative to the vessel about a central axis extending through the inner chamber;
   a shaft positioned within the inner chamber, the shaft comprising an opening defining a first inlet for introducing a liquid into the inner chamber;
   a removable flange which is operatively connected to the shaft, wherein the scaffold is attached to the flange, and wherein the flange is configured to rotate with the scaffold about the central axis;
   one or more mixing elements that are connected to the flange such that they are positioned within the outer chamber and co-rotate with the scaffold to enhance fluid motion and mixing in the outer chamber;
   a first outlet in fluid communication with the inner chamber; and
   an opening in fluid communication with the outer chamber for introducing and/or removing a liquid from the outer chamber.

2. A bioreactor as in claim 1, wherein the opening in the shaft defining the first inlet is radially positioned with respect to a longitudinal axis of the shaft.

3. A bioreactor as in claim 1, further comprising a support structure coupled to the shaft, wherein the support structure comprises an opening defining the first outlet.

4. A bioreactor as in claim 1, wherein the inner chamber and the outer chamber are co-axially arranged with respect to each other.

5. A bioreactor as in claim 1, wherein at least a portion of the scaffold comprises a decellularized tissue construct.

6. A bioreactor as in claim 1, wherein the scaffold is non-porous.

7. A bioreactor as in claim 1, wherein the scaffold is porous.

8. A bioreactor as in claim 1, wherein the scaffold includes a first cell type and a second cell type.

9. A bioreactor as in claim 8, wherein the first cell type is positioned on the outer wall of the inner chamber and the second cell type is positioned on the inner wall of the outer chamber.

10. A bioreactor as in claim 1, further comprising a first pump in fluid communication with the inner chamber.

11. A bioreactor as in claim 10, further comprising a second pump in fluid communication with the outer chamber.

12. A bioreactor as in claim 1, wherein the scaffold supports and includes a tissue attached thereto.

13. A bioreactor as in claim 1, wherein the scaffold supports and includes an organ attached thereto.

* * * * *